United States Patent
Nutt et al.

(10) Patent No.: US 11,300,695 B2
(45) Date of Patent: Apr. 12, 2022

(54) TIME-RESOLVED POSITRON EMISSION TOMOGRAPHY ENCODER SYSTEM FOR PRODUCING EVENT-BY-EVENT, REAL-TIME, HIGH RESOLUTION, THREE-DIMENSIONAL POSITRON EMISSION TOMOGRAPHIC IMAGE WITHOUT THE NECESSITY OF PERFORMING IMAGE RECONSTRUCTION

(71) Applicants: Ronald Nutt, Miami, FL (US); Lynda J. Nutt, Miami, FL (US)

(72) Inventors: Ronald Nutt, Miami, FL (US); Lynda J. Nutt, Miami, FL (US)

( * ) Notice: Subject to any disclaimer, the term of this patent is extended or adjusted under 35 U.S.C. 154(b) by 0 days.

(21) Appl. No.: 17/340,485

(22) Filed: Jun. 7, 2021

(65) Prior Publication Data

US 2021/0333422 A1 Oct. 28, 2021

Related U.S. Application Data

(63) Continuation-in-part of application No. 17/093,095, filed on Nov. 9, 2020, now Pat. No. 11,054,534, (Continued)

(51) Int. Cl.
*G01T 1/29* (2006.01)
*A61B 6/03* (2006.01)

(52) U.S. Cl.
CPC .......... *G01T 1/2985* (2013.01); *A61B 6/037* (2013.01)

(58) Field of Classification Search
CPC .............................. G01T 1/2985; A61B 6/037
(Continued)

(56) References Cited

U.S. PATENT DOCUMENTS 3,541,448 A 11/1970 Nutt
4,559,597 A * 12/1985 Mullani ............... G01T 1/2985
250/363.03
(Continued)

FOREIGN PATENT DOCUMENTS

CN 100342826 10/2007
CN 102316807 1/2012
(Continued)

OTHER PUBLICATIONS

US 8,481,946 B2, 07/2013, Rousso et al. (withdrawn)
(Continued)

*Primary Examiner* — David P Porta
*Assistant Examiner* — Gisselle M Gutierrez
(74) *Attorney, Agent, or Firm* — Pitts & Lake, P.C.

(57) ABSTRACT

A Time-Resolved PET imaging system for producing an event-by-event, real-time, high resolution, three-dimensional positron emission tomographic images without performing sinogram formation or image reconstruction. The third dimension is provided by measuring the ΔT between the arrival times of gamma rays from a positron event being detected by two cooperating detectors. In order to determine the location of a positron event along the lines of response, the measurement includes a fast scintillator, constant fraction discriminator and the digital intervalometer. The arrival time of each photon in the annihilation process is recorded with respect to a clock frequency with picosecond resolution. This approach requires significantly fewer positron events, thus requiring fewer detectors, thereby resulting in an gamma event-by-gamma event, real-time TPET imaging system that is more efficient and more economical to produce than conventional PET systems.

29 Claims, 12 Drawing Sheets

Related U.S. Application Data which is a continuation-in-part of application No. 16/857,499, filed on Apr. 24, 2020, now abandoned.

(58) Field of Classification Search
USPC .................................................. 250/363.04
See application file for complete search history.

(56) References Cited

U.S. PATENT DOCUMENTS

| | | | |
|---|---|---|---|
| 6,490,476 B1 | 12/2002 | Townsend et al. | |
| 6,590,213 B2 | 7/2003 | Wollenweber | |
| 6,661,865 B1 | 12/2003 | Popilock | |
| 6,670,614 B1 | 12/2003 | Plut et al. | |
| 6,774,358 B2 | 8/2004 | Hamill et al. | |
| 6,807,247 B2 | 10/2004 | Krishnan et al. | |
| 6,810,103 B1 | 10/2004 | Tybinkowski et al. | |
| 6,831,961 B1 | 12/2004 | Tybinkowski et al. | |
| 6,852,980 B2 | 2/2005 | Jones et al. | |
| 6,876,718 B2 | 4/2005 | Tang | |
| 6,885,886 B2 | 4/2005 | Bauch et al. | |
| 6,896,234 B2 | 5/2005 | Henley et al. | |
| 6,915,004 B2 | 7/2005 | Newport et al. | |
| 6,920,196 B2 | 7/2005 | Ueno et al. | |
| 6,928,142 B2 | 8/2005 | Shao et al. | |
| 6,950,542 B2 | 9/2005 | Roesch et al. | |
| 6,956,925 B1 | 10/2005 | Hoffman | |
| 6,961,606 B2 | 11/2005 | DeSilets et al. | |
| 6,963,768 B2 | 11/2005 | Ho et al. | |
| 6,965,661 B2 | 11/2005 | Kojima | |
| 6,976,784 B2 | 12/2005 | Kojima et al. | |
| 6,990,222 B2 | 1/2006 | Arnold | |
| 7,087,903 B2 | 8/2006 | Balan et al. | |
| 7,103,233 B2 | 9/2006 | Stearns | |
| 7,136,450 B2 | 11/2006 | Ying et al. | |
| 7,136,692 B2 | 11/2006 | Graw | |
| 7,138,635 B2 | 11/2006 | Heismann | |
| 7,149,565 B2 | 12/2006 | Kojima et al. | |
| 7,154,096 B2 | 12/2006 | Amano | |
| 7,190,991 B2 | 3/2007 | Cable et al. | |
| 7,194,062 B2 | 3/2007 | Balan et al. | |
| 7,209,579 B1 | 4/2007 | Weisenberger et al. | |
| 7,251,523 B2 | 7/2007 | Kojima et al. | |
| 7,254,438 B2 | 8/2007 | DeSilets et al. | |
| 7,265,356 B2 | 9/2007 | Pelizzari et al. | |
| 7,283,604 B2 | 10/2007 | De Man et al. | |
| 7,292,673 B2 | 11/2007 | Kröner et al. | |
| 7,292,721 B2 | 11/2007 | Arnold | |
| 7,297,958 B2 | 11/2007 | Kojima et al. | |
| 7,323,689 B2 | 1/2008 | Hawman | |
| 7,348,564 B2 | 3/2008 | Wollenweber et al. | |
| 7,374,337 B2 | 5/2008 | Yunker | |
| 7,382,851 B2 | 6/2008 | Inoue et al. | |
| 7,397,934 B2 | 7/2008 | Bloch et al. | |
| 7,412,027 B2 | 8/2008 | Yakubovsky et al. | |
| 7,412,280 B2 | 8/2008 | Hertel et al. | |
| 7,424,142 B2 | 9/2008 | Arnold | |
| 7,447,345 B2 | 11/2008 | Shanmugam et al. | |
| 7,465,927 B2 | 12/2008 | Panin et al. | |
| 7,507,968 B2 | 3/2009 | Wollenweber et al. | |
| 7,518,114 B2 | 4/2009 | Ganin et al. | |
| 7,550,728 B2 | 6/2009 | Spahn | |
| 7,558,439 B2 | 7/2009 | Weese et al. | |
| 7,564,945 B2 | 7/2009 | Kim | |
| 7,602,965 B2 | 10/2009 | Hong et al. | |
| 7,613,492 B2 | 11/2009 | Altman et al. | |
| 7,627,078 B2 | 12/2009 | Hsieh et al. | |
| 7,627,082 B2 | 12/2009 | Kojima et al. | |
| 7,634,048 B2 | 12/2009 | Kojima et al. | |
| 7,635,847 B2 | 12/2009 | DiFilippo | |
| 7,640,607 B2 | 1/2010 | Guertin et al. | |
| 7,652,256 B2 | 1/2010 | Lusser | |
| 7,653,228 B2 | 1/2010 | Katscher et al. | |
| 7,676,073 B2 | 3/2010 | Hamill et al. | |
| 7,683,338 B2 | 3/2010 | Ueno et al. | |
| 7,714,291 B2 | 5/2010 | Thielemans | |
| 7,737,972 B2 | 6/2010 | Seppi | |
| 7,738,944 B2 | 6/2010 | Ho et al. | |
| 7,756,307 B2 | 7/2010 | Thielemans | |
| 7,787,675 B2 | 8/2010 | Pan et al. | |
| 7,813,535 B2 | 10/2010 | Florin et al. | |
| 7,813,782 B2 | 10/2010 | Cable et al. | |
| 7,826,889 B2 | 11/2010 | David et al. | |
| 7,838,838 B2 | 11/2010 | Rousso et al. | |
| 7,840,093 B2 | 11/2010 | Fu et al. | |
| 7,869,860 B2 | 1/2011 | Kinahan et al. | |
| 7,872,235 B2 | 1/2011 | Rousso et al. | |
| 7,881,773 B2 | 2/2011 | Cable et al. | |
| 7,935,055 B2 | 5/2011 | Burckhardt | |
| 7,941,203 B2 | 5/2011 | Zheng et al. | |
| 7,968,851 B2 | 6/2011 | Rousso et al. | |
| 7,983,380 B2 | 7/2011 | Guertin et al. | |
| 7,986,763 B2 | 7/2011 | Kojima et al. | |
| 7,991,115 B2 | 8/2011 | Matsuzawa et al. | |
| 8,000,773 B2 | 8/2011 | Rousso et al. | |
| 8,010,184 B2 | 8/2011 | Avila et al. | |
| 8,036,731 B2 | 10/2011 | Kimchy et al. | |
| 8,055,329 B2 | 11/2011 | Kimchy et al. | |
| 8,064,981 B2 | 11/2011 | Eberler et al. | |
| 8,090,431 B2 | 1/2012 | Wang et al. | |
| 8,094,894 B2 | 1/2012 | Nagler et al. | |
| 8,111,886 B2 | 2/2012 | Rousso et al. | |
| 8,116,427 B2 | 2/2012 | Kojima et al. | |
| 8,131,040 B2 | 3/2012 | Koehler et al. | |
| 8,139,713 B2 | 3/2012 | Janbakhsh | |
| 8,150,192 B2 | 4/2012 | Niemeyer et al. | |
| 8,204,500 B2 | 6/2012 | Weintraub et al. | |
| 8,217,937 B2 | 7/2012 | Yeoh et al. | |
| 8,259,899 B2 | 9/2012 | Vaquero López | |
| 8,280,124 B2 | 10/2012 | Dichterman et al. | |
| 8,290,303 B2 | 10/2012 | Washburn et al. | |
| 8,303,505 B2 | 11/2012 | Webler et al. | |
| 8,338,788 B2 | 12/2012 | Zilberstein et al. | |
| 8,415,630 B2 | 4/2013 | Ross et al. | |
| 8,423,125 B2 | 4/2013 | Rousso et al. | |
| 8,445,851 B2 | 5/2013 | Rousso et al. | |
| 8,489,176 B1 | 7/2013 | Ben-David et al. | |
| 8,492,725 B2 | 7/2013 | Zilberstein et al. | |
| 8,520,797 B2 | 8/2013 | Yamada | |
| 8,521,253 B2 | 8/2013 | Melman | |
| 8,565,860 B2 | 10/2013 | Kimchy et al. | |
| 8,571,881 B2 | 10/2013 | Rousso et al. | |
| 8,577,114 B2 | 11/2013 | Faul et al. | |
| 8,586,932 B2 | 11/2013 | Rousso et al. | |
| 8,594,404 B2 | 12/2013 | Yamaya et al. | |
| 8,600,124 B2 | 12/2013 | Arnaud et al. | |
| 8,606,349 B2 | 12/2013 | Rousso et al. | |
| 8,610,075 B2 | 12/2013 | Rousso et al. | |
| 8,611,628 B2 | 12/2013 | Hu et al. | |
| 8,615,405 B2 | 12/2013 | Rousso et al. | |
| 8,620,046 B2 | 12/2013 | Nagler et al. | |
| 8,620,679 B2 | 12/2013 | Rousso et al. | |
| 8,625,870 B2 | 1/2014 | Zamyatin et al. | |
| 8,639,009 B2 | 1/2014 | Lang et al. | |
| 8,644,910 B2 | 2/2014 | Rousso et al. | |
| 8,676,292 B2 | 3/2014 | Rousso et al. | |
| 8,693,741 B2 | 4/2014 | Declerck | |
| 8,698,087 B2 * | 4/2014 | Surti | G01T 1/00 250/363.04 |
| 8,729,480 B2 | 5/2014 | Seidel et al. | |
| 8,748,826 B2 | 6/2014 | Rousso et al. | |
| 8,748,827 B2 | 6/2014 | Zilberstein et al. | |
| 8,767,908 B2 | 7/2014 | Leahy et al. | |
| 8,781,191 B2 | 7/2014 | Lang et al. | |
| 8,818,484 B2 | 8/2014 | Liew et al. | |
| 8,837,793 B2 | 9/2014 | Rousso et al. | |
| 8,894,974 B2 | 11/2014 | Rousso et al. | |
| 8,909,325 B2 | 12/2014 | Kimchy et al. | |
| 8,913,818 B2 | 12/2014 | Lang et al. | |
| 8,938,280 B2 | 1/2015 | Harvey | |
| 8,939,917 B2 | 1/2015 | Vargas | |
| 8,941,071 B1 | 1/2015 | Stearns | |
| 8,965,075 B2 | 2/2015 | Arnaud et al. | |
| 8,965,087 B2 | 2/2015 | Arnaud et al. | |
| 8,971,658 B2 | 3/2015 | Lin et al. | |

(56) References Cited

U.S. PATENT DOCUMENTS

| | | |
|---|---|---|
| 8,977,026 B2 | 3/2015 | Bar-Shalev |
| 8,989,845 B2 | 3/2015 | Brinks et al. |
| 9,008,758 B2 | 4/2015 | Cable et al. |
| 9,014,330 B2 | 4/2015 | Takayama |
| 9,029,787 B2 | 5/2015 | Yamaya et al. |
| 9,031,299 B2 | 5/2015 | Brown et al. |
| 9,040,016 B2 | 5/2015 | Rousso et al. |
| 9,063,203 B2 | 6/2015 | Martin et al. |
| 9,155,501 B2 | 10/2015 | Lang et al. |
| 9,155,514 B2 | 10/2015 | Panin et al. |
| 9,179,882 B2 | 11/2015 | Wiebelitz |
| 9,262,844 B2 | 2/2016 | Hu et al. |
| 9,267,955 B2 | 2/2016 | Lang et al. |
| 9,269,166 B2 | 2/2016 | Hansis et al. |
| 9,275,451 B2 | 3/2016 | Ben-Haim et al. |
| 9,275,469 B2 | 3/2016 | Lang et al. |
| 9,305,377 B2 | 4/2016 | Olivier et al. |
| 9,316,743 B2 | 4/2016 | Rousso et al. |
| 9,330,458 B2 | 5/2016 | Star-Lack |
| 9,349,207 B2 | 5/2016 | Hu et al. |
| 9,370,333 B2 | 6/2016 | Nagler et al. |
| 9,460,506 B2 | 10/2016 | Arnaud et al. |
| 9,460,508 B2 | 10/2016 | Gkanatsios et al. |
| 9,460,510 B2 | 10/2016 | Hermosillo Valadez et al. |
| 9,462,981 B2 | 10/2016 | Padwa et al. |
| 9,470,801 B2 | 10/2016 | Ziv et al. |
| 9,498,167 B2 | 11/2016 | Mostafavi et al. |
| 9,498,175 B2 | 11/2016 | Stein et al. |
| 9,549,709 B2 | 1/2017 | DeFreitas et al. |
| 9,682,159 B2 | 6/2017 | Wiebelitz |
| 9,767,551 B2 | 9/2017 | Lang et al. |
| 9,814,437 B2 | 11/2017 | Mitchell et al. |
| 9,851,888 B2 | 12/2017 | Gkanatsios et al. |
| 9,872,664 B1 | 1/2018 | Jin et al. |
| 9,943,274 B2 | 4/2018 | Rousso et al. |
| 9,943,278 B2 | 4/2018 | Nagler et al. |
| 9,974,494 B2 | 5/2018 | Mostafavi et al. |
| 10,004,650 B2 | 6/2018 | Guertin et al. |
| 10,108,329 B2 | 10/2018 | Gkanatsios et al. |
| 10,136,865 B2 | 11/2018 | Rousso et al. |
| 10,147,206 B2 | 12/2018 | Li et al. |
| 10,188,356 B2 | 1/2019 | Guertin et al. |
| 10,194,875 B2 | 2/2019 | DeFreitas et al. |
| 10,198,793 B2 | 2/2019 | Ohishi et al. |
| 10,282,871 B2 | 5/2019 | Wang et al. |
| 10,296,199 B2 | 5/2019 | Gkanatsios et al. |
| 10,342,504 B2 | 7/2019 | Star-Lack et al. |
| 10,410,379 B2 | 9/2019 | Sun et al. |
| 10,413,255 B2 | 9/2019 | Stein et al. |
| 10,426,424 B2 | 10/2019 | Crotty et al. |
| 10,441,226 B2 | 10/2019 | Guertin et al. |
| 10,452,252 B2 | 10/2019 | Gkanatsios et al. |
| 10,565,746 B2 | 2/2020 | Wang et al. |
| 10,624,599 B2 | 4/2020 | Feng et al. |
| 10,638,994 B2 | 5/2020 | DeFreitas et al. |
| 10,660,598 B2 | 5/2020 | Katsumata |
| 10,690,782 B2 | 6/2020 | Wang et al. |
| 2002/0183607 A1 | 12/2002 | Bauch et al. |
| 2002/0191734 A1 | 12/2002 | Kojima et al. |
| 2003/0076925 A1 | 4/2003 | DeSilets et al. |
| 2003/0078488 A1 | 4/2003 | DeSilets et al. |
| 2003/0095695 A1 | 5/2003 | Arnold |
| 2003/0108147 A1 | 6/2003 | Kojima et al. |
| 2003/0118155 A1 | 6/2003 | Ueno et al. |
| 2003/0153828 A1 | 8/2003 | Kojima et al. |
| 2003/0161521 A1 | 8/2003 | Newport et al. |
| 2003/0178559 A1 | 9/2003 | Hamill et al. |
| 2003/0194050 A1 | 10/2003 | Eberhard et al. |
| 2003/0216631 A1 | 11/2003 | Bloch et al. |
| 2003/0216637 A1 | 11/2003 | Ho et al. |
| 2004/0013290 A1 | 1/2004 | Krishnan et al. |
| 2004/0044282 A1 | 3/2004 | Mixon et al. |
| 2004/0062345 A1 | 4/2004 | Kojima et al. |
| 2004/0068167 A1 | 4/2004 | Hsieh et al. |
| 2004/0076262 A1 | 4/2004 | Shao et al. |
| 2004/0086199 A1 | 5/2004 | Stearns |
| 2004/0092814 A1 | 5/2004 | Hsieh |
| 2004/0174948 A1 | 9/2004 | Kojima et al. |
| 2004/0217292 A1 | 11/2004 | Moyers et al. |
| 2004/0249260 A1 | 12/2004 | Wang et al. |
| 2004/0260171 A1 | 12/2004 | Graumann |
| 2004/0260176 A1 | 12/2004 | Wollenweber et al. |
| 2004/0264629 A1 | 12/2004 | Tang |
| 2005/0004452 A1 | 1/2005 | Hertel et al. |
| 2005/0015004 A1 | 1/2005 | Hertel et al. |
| 2005/0028482 A1 | 2/2005 | Cable et al. |
| 2005/0065421 A1 | 3/2005 | Burckhardt |
| 2005/0067578 A1 | 3/2005 | Ueno et al. |
| 2005/0082487 A1 | 4/2005 | Amano |
| 2005/0098735 A1 | 5/2005 | Heismann |
| 2005/0109943 A1 | 5/2005 | Vaquero et al. |
| 2005/0127301 A1 | 6/2005 | Balan et al. |
| 2005/0129295 A1 | 6/2005 | Shanmugam et al. |
| 2005/0152492 A1 | 7/2005 | Yakubovsky et al. |
| 2005/0161606 A1 | 7/2005 | Balan et al. |
| 2005/0171423 A1 | 8/2005 | Ho et al. |
| 2005/0213705 A1 | 9/2005 | Hoffman |
| 2005/0226527 A1 | 10/2005 | Weese et al. |
| 2005/0276373 A1 | 12/2005 | Ying et al. |
| 2005/0287065 A1 | 12/2005 | Suddarth |
| 2006/0004274 A1 | 1/2006 | Hawman |
| 2006/0013459 A1 | 1/2006 | Katscher et al. |
| 2006/0036160 A1 | 2/2006 | Altman et al. |
| 2006/0050839 A1 | 3/2006 | Balan et al. |
| 2006/0088198 A1 | 4/2006 | Arnold |
| 2006/0091315 A1 | 5/2006 | Hawman |
| 2006/0093217 A1 | 5/2006 | Hong et al. |
| 2006/0097175 A1 | 5/2006 | Ganin et al. |
| 2006/0109959 A1 | 5/2006 | Kroner et al. |
| 2006/0113482 A1 | 6/2006 | Pelizzari et al. |
| 2006/0171883 A1 | 8/2006 | Phillips et al. |
| 2006/0173297 A1 | 8/2006 | Popescu |
| 2006/0180766 A1 | 8/2006 | Difilippo |
| 2006/0214108 A1 | 9/2006 | Balan et al. |
| 2006/0235294 A1 | 10/2006 | Florin et al. |
| 2006/0253013 A1 | 11/2006 | Cable et al. |
| 2006/0258941 A1 | 11/2006 | Cable et al. |
| 2006/0285647 A1 | 12/2006 | Yunker |
| 2007/0003010 A1 | 1/2007 | Guertin et al. |
| 2007/0003021 A1 | 1/2007 | Guertin et al. |
| 2007/0014391 A1 | 1/2007 | Mostafavi et al. |
| 2007/0057191 A1 | 3/2007 | Ueno et al. |
| 2007/0064865 A1 | 3/2007 | Inoue et al. |
| 2007/0081703 A1 | 4/2007 | Johnson |
| 2007/0081704 A1 | 4/2007 | Pan et al. |
| 2007/0102642 A1 | 5/2007 | Spahn |
| 2007/0116170 A1 | 5/2007 | De Man et al. |
| 2007/0127789 A1 | 6/2007 | Hoppel et al. |
| 2007/0131858 A1 | 6/2007 | Wollenweber et al. |
| 2007/0147589 A1 | 6/2007 | Thielemans |
| 2007/0167697 A1 | 7/2007 | Avila et al. |
| 2007/0167716 A1 | 7/2007 | Kinahan et al. |
| 2007/0221850 A1 | 9/2007 | Panin et al. |
| 2007/0223651 A1 | 9/2007 | Wagenaar et al. |
| 2007/0253529 A1 | 11/2007 | Seppi |
| 2008/0001089 A1 | 1/2008 | Lusser |
| 2008/0008366 A1 | 1/2008 | Desh et al. |
| 2008/0033291 A1 | 2/2008 | Rousso et al. |
| 2008/0056549 A1 | 3/2008 | Hamill et al. |
| 2008/0058613 A1 | 3/2008 | Lang et al. |
| 2008/0081985 A1 | 4/2008 | Zheng et al. |
| 2008/0095414 A1 | 4/2008 | Desh et al. |
| 2008/0118182 A1 | 5/2008 | Koole |
| 2008/0130970 A1 | 6/2008 | Niemeyer et al. |
| 2008/0137804 A1 | 6/2008 | Kojima et al. |
| 2008/0139924 A1 | 6/2008 | Eberler et al. |
| 2008/0159612 A1 | 7/2008 | Fu et al. |
| 2008/0161703 A1 | 7/2008 | Houben |
| 2008/0205588 A1 | 8/2008 | Kim |
| 2008/0224050 A1 | 9/2008 | Thieleman |
| 2008/0240548 A1 | 10/2008 | Yeoh |
| 2008/0260284 A1 | 10/2008 | Lin et al. |
| 2008/0273659 A1 | 11/2008 | Guertin et al. |
| 2008/0277591 A1 | 11/2008 | Shahar et al. |

(56) References Cited

U.S. PATENT DOCUMENTS

| | | |
|---|---|---|
| 2008/0319305 A1 | 12/2008 | Martin et al. |
| 2009/0065699 A1 | 3/2009 | Vaquero et al. |
| 2009/0067700 A1 | 3/2009 | Maton et al. |
| 2009/0091567 A1 | 4/2009 | Fu et al. |
| 2009/0092229 A1 | 4/2009 | Kojima et al. |
| 2009/0154647 A1 | 6/2009 | Matsuzawa et al. |
| 2009/0213983 A1 | 8/2009 | Vaquero Lopez et al. |
| 2010/0001200 A1 | 1/2010 | Ben-Haim et al. |
| 2010/0092052 A1 | 4/2010 | Declerck et al. |
| 2010/0098312 A1 | 4/2010 | Leahy et al. |
| 2010/0106004 A1 | 4/2010 | Harvey |
| 2010/0128956 A1 | 5/2010 | Yamaya et al. |
| 2010/0158336 A1 | 6/2010 | Motomura et al. |
| 2010/0239134 A1 | 9/2010 | Koehler et al. |
| 2011/0036360 A1 | 2/2011 | Lang et al. |
| 2011/0040168 A1 | 2/2011 | Arnaud et al. |
| 2011/0058722 A1 | 3/2011 | Hu et al. |
| 2011/0092813 A1 | 4/2011 | Cable et al. |
| 2011/0105885 A1 | 5/2011 | Liew et al. |
| 2011/0129061 A1 | 6/2011 | Janbakhsh |
| 2011/0142367 A1 | 6/2011 | Stearns et al. |
| 2011/0243847 A1 | 8/2011 | Wiebelitz |
| 2011/0299656 A1 | 12/2011 | Yamada |
| 2012/0046544 A1 | 2/2012 | Inoue |
| 2012/0070057 A1 | 3/2012 | Zhang et al. |
| 2012/0148138 A1 | 6/2012 | Faul et al. |
| 2012/0161014 A1 | 6/2012 | Yamaya et al. |
| 2012/0256092 A1 | 10/2012 | Zingerman |
| 2013/0003918 A1 | 1/2013 | Takayama |
| 2013/0009063 A1 | 1/2013 | Henseler et al. |
| 2013/0208971 A1 | 8/2013 | Brown et al. |
| 2013/0287278 A1 | 10/2013 | Olivier et al. |
| 2013/0322717 A1 | 12/2013 | Bar-Shalev |
| 2013/0322720 A1 | 12/2013 | Hu et al. |
| 2014/0151529 A1 | 6/2014 | Steiner et al. |
| 2014/0294263 A1 | 10/2014 | Hermosillo Valadez et al. |
| 2015/0021488 A1 | 1/2015 | Stearns |
| 2015/0036789 A1 | 2/2015 | Panin et al. |
| 2015/0119703 A1 | 4/2015 | Mitchell et al. |
| 2015/0170359 A1 | 6/2015 | Star-Lack et al. |
| 2015/0178918 A1 | 6/2015 | Arnaud et al. |
| 2015/0201891 A1 | 7/2015 | Padwa et al. |
| 2015/0269711 A1 | 9/2015 | Ohishi et al. |
| 2015/0289829 A1 | 10/2015 | Yamada et al. |
| 2017/0365073 A1 | 12/2017 | Sun et al. |
| 2018/0184994 A1 | 7/2018 | Keertikuma |

FOREIGN PATENT DOCUMENTS

| | | |
|---|---|---|
| CN | 102317975 | 1/2012 |
| CN | 102525521 | 7/2012 |
| CN | 101756698 | 9/2012 |
| CN | 102727238 | 10/2012 |
| CN | 101778600 | 2/2013 |
| CN | 103054600 | 4/2013 |
| CN | 103533892 | 1/2014 |
| CN | 103800019 | 5/2014 |
| CN | 102316807 | 6/2014 |
| CN | 102317975 | 2/2015 |
| CN | 103054600 | 3/2015 |
| CN | 101011259 | 4/2015 |
| CN | 103800019 | 7/2015 |
| CN | 105193442 | 12/2015 |
| CN | 103533892 | 8/2016 |
| CN | 106097409 | 11/2016 |
| CN | 106097409 | 9/2019 |
| DE | 102004049915 | 5/2006 |
| EP | 1773198 | 4/2007 |
| EP | 1836961 | 9/2007 |
| EP | 1773198 | 8/2009 |
| EP | 2201895 | 6/2010 |
| EP | 2398390 | 4/2015 |
| EP | 1792569 | 8/2015 |
| EP | 2974663 | 1/2016 |
| EP | 3258444 A1 | 12/2017 |
| EP | 2289048 B1 | 2/2019 |
| EP | 2706917 B1 | 6/2019 |
| EP | 2974663 B1 | 6/2019 |
| FR | 2857129 | 1/2005 |
| JP | 2005193018 | 7/2005 |
| JP | 2011521224 | 7/2011 |
| JP | 4758910 | 8/2011 |
| NL | 1033813 | 12/2008 |
| RU | 2284150 | 9/2006 |
| RU | 2427037 | 8/2011 |
| WO | WO2005029507 | 3/2005 |
| WO | WO2006006966 | 1/2006 |
| WO | WO2005029507 | 2/2006 |
| WO | WO2008129666 | 10/2008 |
| WO | WO2009022271 | 2/2009 |
| WO | WO2009138898 A1 | 11/2009 |
| WO | WO2010095062 | 8/2010 |
| WO | WO2011094811 | 8/2011 |
| WO | WO2012153219 | 11/2012 |
| WO | WO2007018646 | 2/2017 |

OTHER PUBLICATIONS

US 8,527,294 B2, 09/2013, Rousso et al. (withdrawn)
Michael E. Phelps, et al.; "Application of Annihialiation Coincidence Detection to Transaxial Reconstruction Tomography"; Journal of Nuclear Medicine, Mar. 1, 1975, 16:210-224.
Schaart, et al.; "LaBr3:Ce and SiPMs for time-of-flight PET: achieving 100 ps coincidence resolving time"; Phys. Med. Biol. 55, Mar. 19, 2010; N179-N189.
Gundacker, et al.; "High-frequence SiPM readout advances measured coincidence time resolution limits in TOF-PET"; Phys. Med. Biol. 64, 5, Feb. 26, 2019.
Acerbi, et al.; "Analysis of single-photon resolution of FBK silicon photomultipliers"; Nuclear Instruments and Methods in Physics Research, 787, 2015; 34-37.
Seifart, et al.; "A Comprehensive Model to Predict the Timing Resolution of SiPM-Based Scintillation Detectors"; IEEE Transactions of Nuclear Science, 59, 1, Feb. 2012, 190-204.
Vinke, et al.; "Optimizing the timing resolution of SiPM sensors for use in TOF-PET detectors"; Nuclear Instruments and Methods in Physics Research, 610, 1, Oct. 21, 2009; 188.
Genat, et al.; "Signal Processing for Pico-second Resolution Timing Measurements"; Physics.ins-det, 5590, 1, Oct. 30, 2008.
Patent Cooperation Treaty, International Search Report, dated Sep. 22, 2021; Form PCT/ISA/220 (revised Jan. 2020).

\* cited by examiner

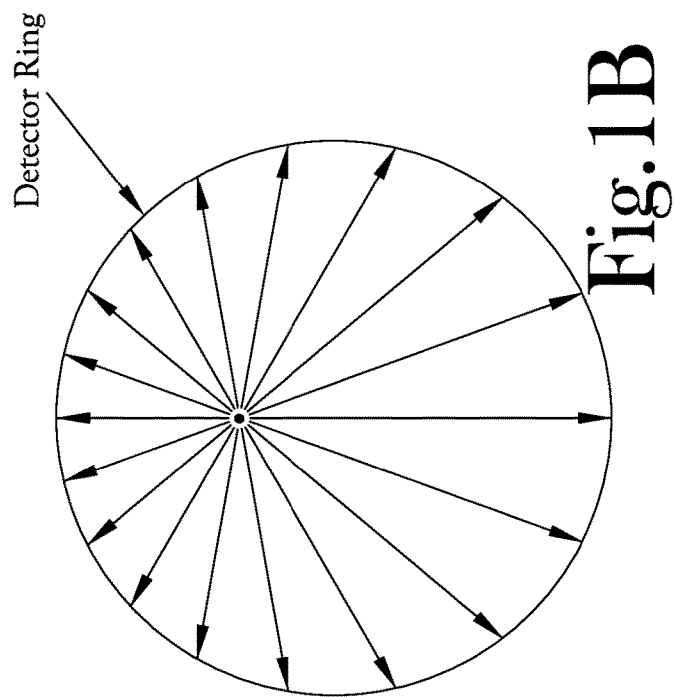
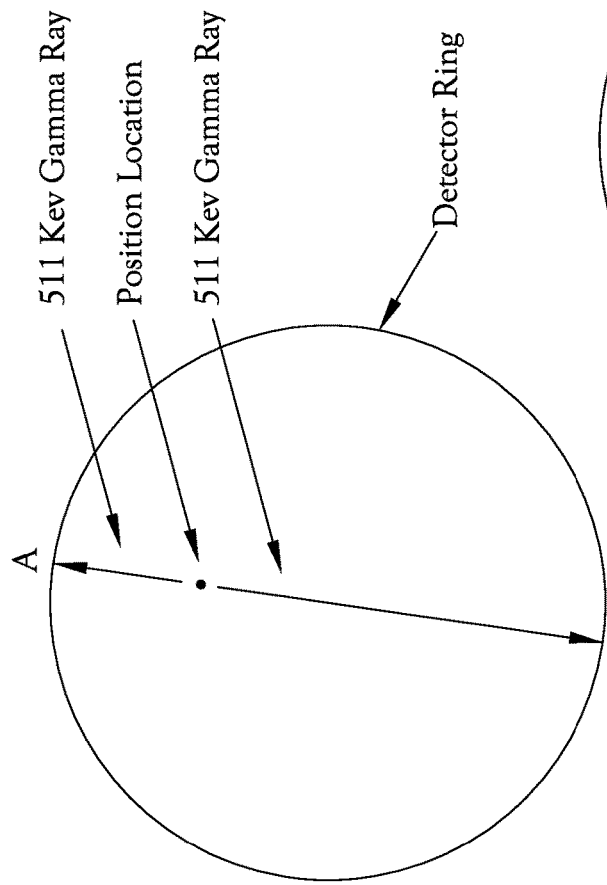
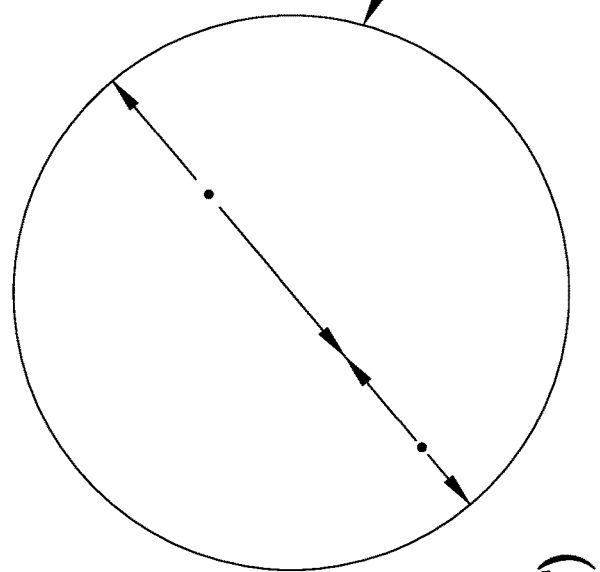
Fig. 1A (PRIOR ART)
Fig. 1B (PRIOR ART)
Fig. 1C (PRIOR ART)

Conventional PET Scanner

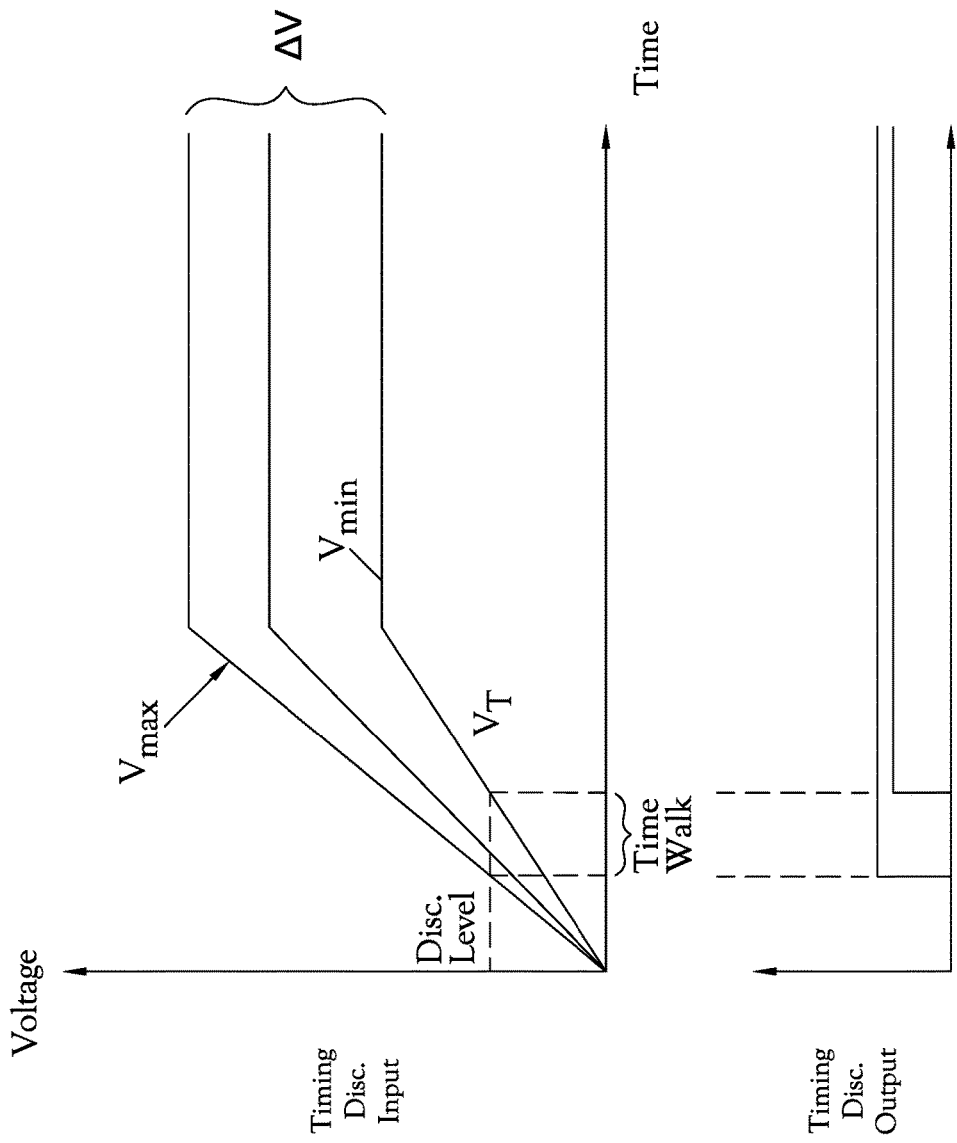
Fig.3 (Prior Art)  Leading Edge Disc. Problem

TIME-RESOLVED POSITRON EMISSION TOMOGRAPHY ENCODER SYSTEM FOR PRODUCING EVENT-BY-EVENT, REAL-TIME, HIGH RESOLUTION, THREE-DIMENSIONAL POSITRON EMISSION TOMOGRAPHIC IMAGE WITHOUT THE NECESSITY OF PERFORMING IMAGE RECONSTRUCTION

CROSS-REFERENCE TO RELATED APPLICATIONS

This application claims the benefit of U.S. Non-Provisional patent application Ser. No. 16/857,499, filed on Apr. 24, 2020, and U.S. Non-Provisional patent application Ser. No. 17/093,095, filed on Nov. 9, 2020, each of which is incorporated herein in its entirety by reference.

STATEMENT REGARDING FEDERALLY SPONSORED RESEARCH OR DEVELOPMENT

Not Applicable

BACKGROUND OF THE INVENTION

1. Field of Invention

The present general inventive concept relates to a new Time-Resolved Positron Emission Tomography system, ("TPET"). More particularly, it relates to a much simpler Time-Resolved PET Imaging System offering event-by-event, i.e., real-time imaging, requiring only a single view, fewer detectors, and producing high resolution PET imagery without the necessity of performing image reconstruction and without the necessity of an additional/simultaneous computed tomography, ("CT"), scan for attenuation correction.

2. Description of the Related Art

When a positron decays it produces two gamma rays that have directions 180 degrees opposed to one another, (see FIG. 1A). While there is a small error in the angle due to the momentum of the positron, for Positron Emission Tomography, ("PET"), imaging it is assumed to be small enough to ignore. In PET imaging the line that is formed by the detection of the two gamma rays is called a "Line of Response", ("LOR"). It is known in the Positron Emission Tomography field that the state-of-the-art photomultiplier and relatively slow scintillators have limited the timing resolution of scintillator based optical detection systems for decades. It is also known that existing PET systems require all views within a plane to form a complete image of the object. These systems utilize software algorithms that attempt to find the intersection of the large number of LORs to form the image. In FIG. 1B, the LORs for a point source are shown. The circle implies detectors that can detect the Gamma rays from the point source. A typical, state-of-the-art, prior art Ring PET tomograph will have several hundred detector elements in the Ring, see e.g., FIG. 1D. In the prior art there will be more than 100,000 LORs in a single Ring. Using this set of LORs to form an image, the LORS must be arranged in an orderly format by a fast computer. The arrangement is called a sinogram and the process is called sorting.

One can see from FIG. 1C that if the image has two locations of positrons the process of finding the intersection of LORs to identify the exact location of the positrons becomes more complicated. A fact is that it always requires two or more LOR intersections to identify a single source of positrons. When one considers several hundred locations of positron events within an image, one understands that it requires the intersection of several million LORs to form an approximate image. The process of interpreting the data of several million LOR's is called "Image Reconstruction". This is well known in the prior art, see e.g., Henseler, U.S. Pub. No. US2013/0009063, (hereinafter "Henseler '063"), which discloses: "After being sorted into parallel projections, the LOR defined by the coincidence events are used to reconstruct a three-dimensional distribution of the positron-emitting radionuclide within the patient." Henseler '063, [0005], emphasis added. Further, Henseler teaches, "Imaging system 812 may use the onset of the gamma interaction to reconstruct a three-dimensional distribution of the positron-emitting radionuclide within the patient and display a useful image to the doctor or operator." Henseler, '063, at paragraph [0051]. The process of image reconstruction requires the use of powerful computers and normally requires several minutes to complete, making it, from a diagnostic perspective, time consuming. FIG. 2A depicts a prior art PET imaging system as illustrated by Henseler '063.

The two major computers that are typically used in state-of-the-art image reconstruction, as illustrated in FIG. 2A, are represented by the box labeled Computer-Readable Medium 806 where the sorting process takes place and the memory of the sinograms are located; further, the processor 810 is the reconstruction processor and typically will be a powerful computer. The reconstruction process will either be a statistical process or a back-projection process but will require several minutes with a fast computer to form an approximate image.

The advent of the Avalanche Photodiode is beginning to replace the photomultiplier and has provided major improvements in time resolution of scintillator systems and in other parameters such as resistance to magnetic fields. The Avalanche Photodiode technology applied to the Silicon photomultiplier (SiPM) has made it possible to measure the time it takes for a gamma ray to travel along a specific line-of-response ("LOR"). In other words, the improved time resolution allows the precise measurement of the location of the annihilation event along the LOR. This time measurement is the foundation for the time-resolved Positron Emission Tomography system disclosed herein and referred to herein as the TPET imaging system. This TPET imaging system should not be confused with existing Time-of-Flight systems, such as illustrated in FIG. 2A and described in Henseler '063, that are presently on the market. For instance, Henseler '063 discloses:

> Time-of-flight (TOF) positron emission tomography (PET) ("TOF-PET") is based on the measurement of the difference $\Delta T$ between the detection times of the two gamma photons arising from the positron annihilation event. This measurement allows the annihilation event to be localized along the LOR with a resolution of about 75-120 mm FWHM, assuming a time resolution of 500-800 ps (picoseconds). Though less accurate than the spatial resolution of the scanner, this approximate localization is effective in reducing the random coincidence rate and in improving both the stability of the reconstruction and the signal-to-noise ratio (SNR), especially when imaging large objects. Thus, in TOF-PET, the "TOF" coordinate, $\Delta T$, is stored together with s and $\varphi$.

Henseler '063 at paragraph [0010].

It is known in the art that use of TOF information in PET has the potential to enable significant improvement in image noise properties, which in turn can increase lesion detection. This concept of TOF has been proposed in the literature and is available commercially, but designs that will produce acceptable high time resolution, a single view, and that use the time information to form the image directly have not been proposed or developed. This disclosure contains a system that optimizes the time resolution of a silicon photomultiplier (SiPM) including the use of a very fast scintillator and has the potential to provide image resolution equal to or better than conventional PET imagery.

The normal LOR is determined by standard block detectors that measure the gamma ray position, both X and Y coordinates, in two-dimensional space. The third dimensional coordinate, Z in an XYZ coordinate system, is then provided by the time measurements of the travel of the coincident gamma rays, and more specifically the difference between the time one gamma ray is detected and the time when the second gamma ray is detected. This time measurement can be made by an analog technique known in the art as Time-to-Amplitude Converter ("TAC"). The TAC measurement is accomplished by the first gamma ray switching a constant current onto a small capacitor and switching the current off by the second gamma ray. The voltage on the capacitor is then proportional to the time difference between the two signals. The problem with this technique is that many events are occurring in a short period of time; and, in order to provide real-time, i.e. gamma event-by-gamma event analysis, the system must be able to measure all of these events, and, in real-time, detect and isolate those events where the time difference falls within the desired field of view. A state-of-the-art analog TAC simply does not have this capability.

Since a gamma ray travels at the speed of light, i.e., 30 centimeters per nanosecond, and gamma rays travel in opposite directions for PET, 15 centimeters from the center corresponds to a time difference of one nanosecond. The reconstructed resolution of conventional PET systems is approximately 5 to 6 millimeters in three dimensions so 6 millimeters along a LOR corresponds to 40 picoseconds. This is the needed time resolution of the TPET imaging system such that Z-coordinate position resolution is equivalent to the existing standard PET imaging systems.

The present PET scanners measure and record the LORs and then perform an image reconstruction by statistically determining the intersection of all LORs with each other. The statistical process requires a very large number of events, and thus, a large number of detectors, and, therefore, is very inefficient. This process requires many more events than does the direct measurement of the TPET imaging system of the present general inventive concept and therefore is much more inefficient than the TPET imaging system disclosed herein. This can be best understood for a simple point source of activity in the field of view where a single TPET measurement can result in an image. If the volume being considered has a complex distribution of activity, it is known in the PET art that the number of events needed for a good image may increase to millions of events for the conventional system.

The time measuring system currently known in the art uses either standard Photomultipliers or SiPM detectors such as the SiPM detectors supplied by Philips or Hamamatsu. The known measurement systems, which utilize an SiPM optical detector and an LSO scintillator, utilize a leading-edge discriminator and a simple frequency counter. It is known that this type of system is not capable of producing event-by-event, i.e., real-time, high resolution performance in the time domain or in the third dimension of the PET system for two additional reasons. The first problem is the leading-edge timing used in the discriminators. This leading-edge technique uses an electronic discriminator that changes states when the leading edge of the pulse exceeds a defined level. The state-of-the art time resolution is 250 picoseconds for the conventional PET system and is used to set the coincidence window for the standard PET system. This time resolution is set primarily by the LSO scintillator being used. It does not appear in the art that there has been any attempt to use this timing information to eliminate the image reconstruction. However, even if this timing information were used in the conventional PET system to eliminate the reconstruction process, the image resolution would be approximately 37 millimeters. Even if the TOF were used to eliminate image reconstruction, the result is an unacceptably low resolution in the diagnostic imaging industry. These problems are addressed in the TPET imaging system disclosed herein.

Further, it is known in the art that time walk associated with leading edge discriminators is undesirable; and that, even in cases in which the amplitude of the light signal does not vary appreciably, residual time walk can have a negative impact on time resolution. As is evident from FIG. 3, if one assumes an input rise time of 9,000 picoseconds, i.e. 9 nanoseconds, the time walk due to pulse height changes can be very significant. In this regard, it is known in the timing area that the input current pulse height can vary V from 30 to 50%. If one assumes the input pulse has a linear rise-time, then the time walk associated with the leading-edge discriminator is given by;

$$\Delta t = \frac{V_{Max}}{V_T} \cdot Risetime \left[ \frac{1}{1 - \Delta V} - 1 \right]$$

Using 40% variation of the current pulse, 9,000 picosecond rise-time, and assuming ratio of 100:1 of VMAX to VT. This ratio is considered by those working in the analog field to be the maximum feasible ratio. Using these parameters in the equation yields:

$$\Delta t = \frac{0.9}{100} \cdot 10^{-8} \left[ \frac{1}{1 - 0.4} - 1 \right] = 60 \text{ ps}$$

For the two detectors that are necessary in a traditional PET system, the time resolution in this example would be the square root of two times 60 ps, or 85 ps. The best resolution reported in the prior art is around 100 ps. From this example, it is apparent that the time uncertainty due to time walk is significant and will have to be significantly reduced, or eliminated, in any practical time-resolved PET imaging system.

Further, a second known time measuring system is the Digital Intervalometer described by the applicant herein in U.S. Pat. No. 3,541,448, which is incorporated herein by reference, and which was issued to the applicant herein on Nov. 17, 1970. This time measurement consists of a digital clock which counts the ticks on an oscillator between a start and a stop signal. In addition, the time between the start and the oscillator is measured by a digital Time-to-Amplitude Converter, ("TAC"), and the difference between the oscillator and the stop signal is also measured with a digital TAC.

The most significant digits of the clock are provided by the digital TAC and added sequentially to the word containing the ticks of the oscillator. If the desired measurement is between a start and the oscillator, which is the case for TPET operation, only one of the TAC interpolators is used to measure the time of arrival of one of the 511 KeV gamma rays.

A time-resolved PET imaging system offering event-by-event, real-time, high resolution imaging utilizing fewer detectors than traditional PET systems, and not requiring image reconstruction, is unavailable in the known art. Accordingly, it is a feature of the present general inventive concept to provide a Time-resolved PET system having a much simpler design than conventional PET imaging systems, therefore resulting in a much lower cost to construct, that provides high-resolution images event-by-event, in real time, and which eliminates the need for a CT scan for attenuation correction. The primary feature of the present general inventive concept is to provide a TPET imaging system that utilizes time measurement information to determine a position along an LOR in order to provide a measurement of a third dimensional coordinate, resulting in near real-time, high resolution three-dimensional imaging in a TPET imaging system having fewer detectors with significantly fewer measured events, i.e., without detecting and measuring millions of events before forming an image. Smaller probes using the TPET concept of the present general inventive concept can be used to image specific organs of the body without introducing artifacts, unlike the present PET systems that require all views around the patient. This allows very practical breast imaging, cardiac imaging, and prostate imaging, to name a few organ systems that could be imaged using the TPET imaging system of the present general inventive concept. Another very significant feature of the TPET is that only one view is required, and this characteristic allows accurate calculation of the attenuation of the gamma rays being emitted from the patient. Known prior art systems require a CT image to correct the attenuation of the gamma rays being emitted. This produces a much more complicated PET system, and therefore a much more expensive system. Accordingly, there is a need for a time-resolved PET System that will produce an event-by-event high resolution, three-dimensional positron emission tomographic image in real-time without either the necessity of performing image reconstruction or requiring the use of a CT image to correct attenuation.

BRIEF SUMMARY OF THE INVENTION

In an exemplary embodiment of the present general inventive concept, a TPET imaging system capable of providing event-by-event, i.e., real-time, high resolution, three-dimensional imagery is provided without the need for image reconstruction or CT correction of the attenuation of gamma rays. Whereas the radiation detectors provide X and Y coordinates, the third dimensional coordinate, i.e. the Z coordinate, is provided by measuring the detection time difference, ("$\Delta T$"), between the gamma rays from a positron event being detected by two gamma ray detectors that are much faster than the scintillator detectors used in the conventional PET system. In order to provide this time measurement in real time, and in a manner that requires detection of significantly fewer events than traditional PET, rather than using a leading-edge timing discriminator and a traditional time encoder to determine a gamma event's location along the LOR, in an exemplary embodiment, TPET imaging system disclosed herein utilizes further electronic circuitry, which both measures the arrival time of each photon in the annihilation process with picosecond resolution and which decreases the time walk to an insignificant contribution of the overall time resolution is utilized. In an exemplary embodiment, decreasing the time walk is accomplished by use of a Constant Fraction Discriminator, ("CFD"), operating in conjunction with the Digital Intervalometer, for performing the time-measuring function, invented by the applicant herein. While the Constant Fraction Discriminator and the Digital Intervalometer could be utilized as discrete circuits, or separate chip sets, in an exemplary embodiment, the Constant Fraction Discriminator and the Digital Intervalometer are embedded on an Application Specific Integrated Circuit ("ASIC"). With this time measurement system, the arrival time of each photon in the annihilation process is recorded with respect to a clock frequency with picosecond resolution. In an exemplary embodiment, this TPET approach, requires significantly fewer gamma events, thus requiring fewer detectors, thereby resulting in a system that is more efficient and more economical to produce. By providing real-time, high resolution, artifact free images, the TPET imaging system of the present general inventive concept allows real-time image comparisons of multiple organs thereby giving the clinician/diagnostician greater understanding of the relationships of multiple organ systems. Also, the system allows the observation in real time of cancer lesions that are being treated by radiation or other means.

BRIEF DESCRIPTION OF THE SEVERAL VIEWS OF THE DRAWINGS

The above-mentioned features of the present general inventive concept will become more clearly understood from the following detailed description of the present general inventive concept read together with the drawings in which:

FIG. 1A illustrates, in a simplified schematic view, the physics of a positron event in which two gamma rays are produced that travel in directions that are 180° opposed to one another;

FIG. 1B illustrates, in a simplified schematic view, Lines of Response, ("LORs"), from a single point source of positrons;

FIG. 1C illustrates, in a simplified schematic view, complications that arise in the process of locating the intersection of LORs to identify the exact location of the positrons if the image has two locations of positrons;

FIG. 3 is chart illustrating the problem of time walk due to pulse height changes common in many of the standard PET systems;

DETAILED DESCRIPTION OF THE INVENTION

Figure 5:
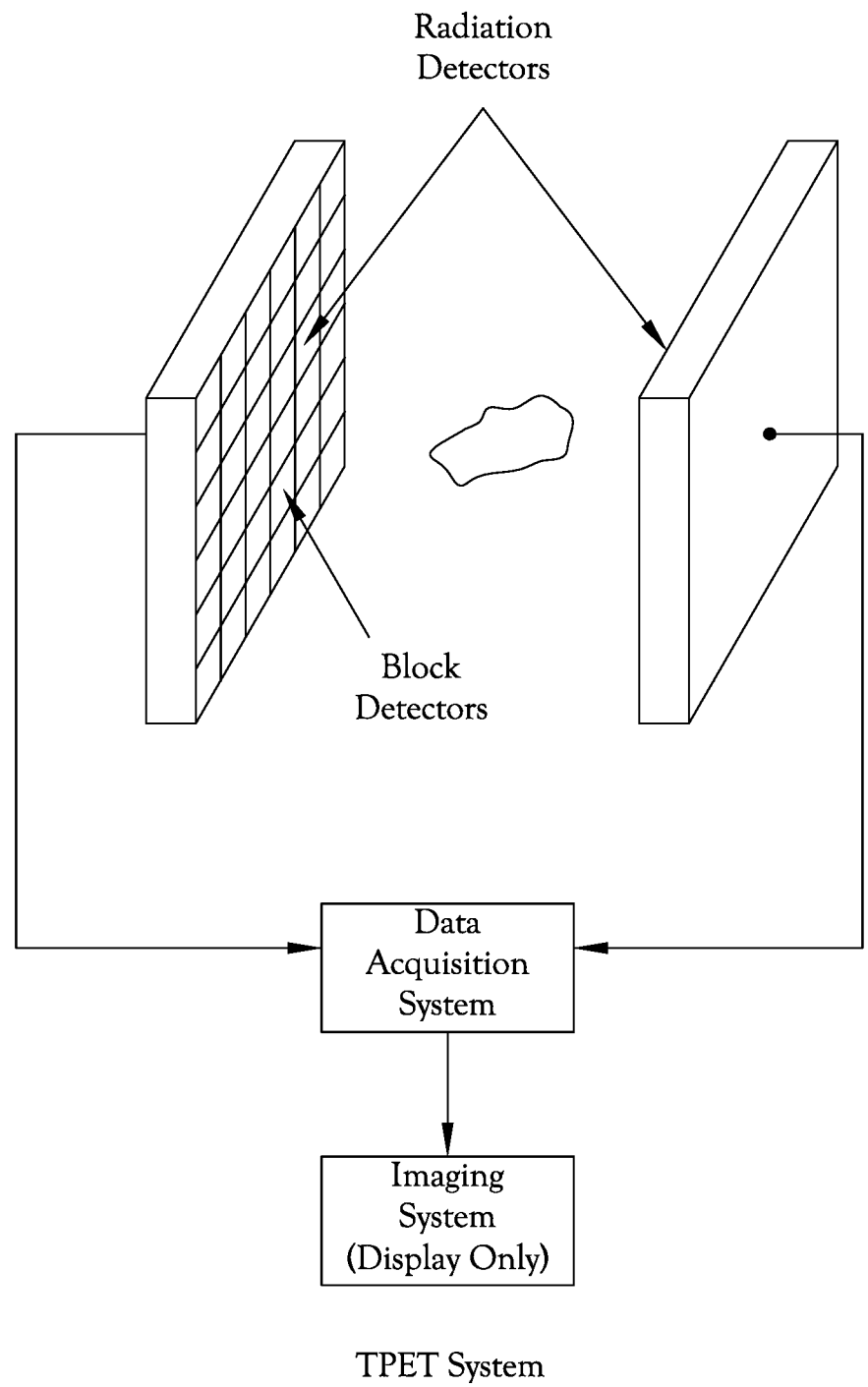
FIG. 5 is a schematic view of the TPET imaging system of the present general inventive concept.
Figure 6A:
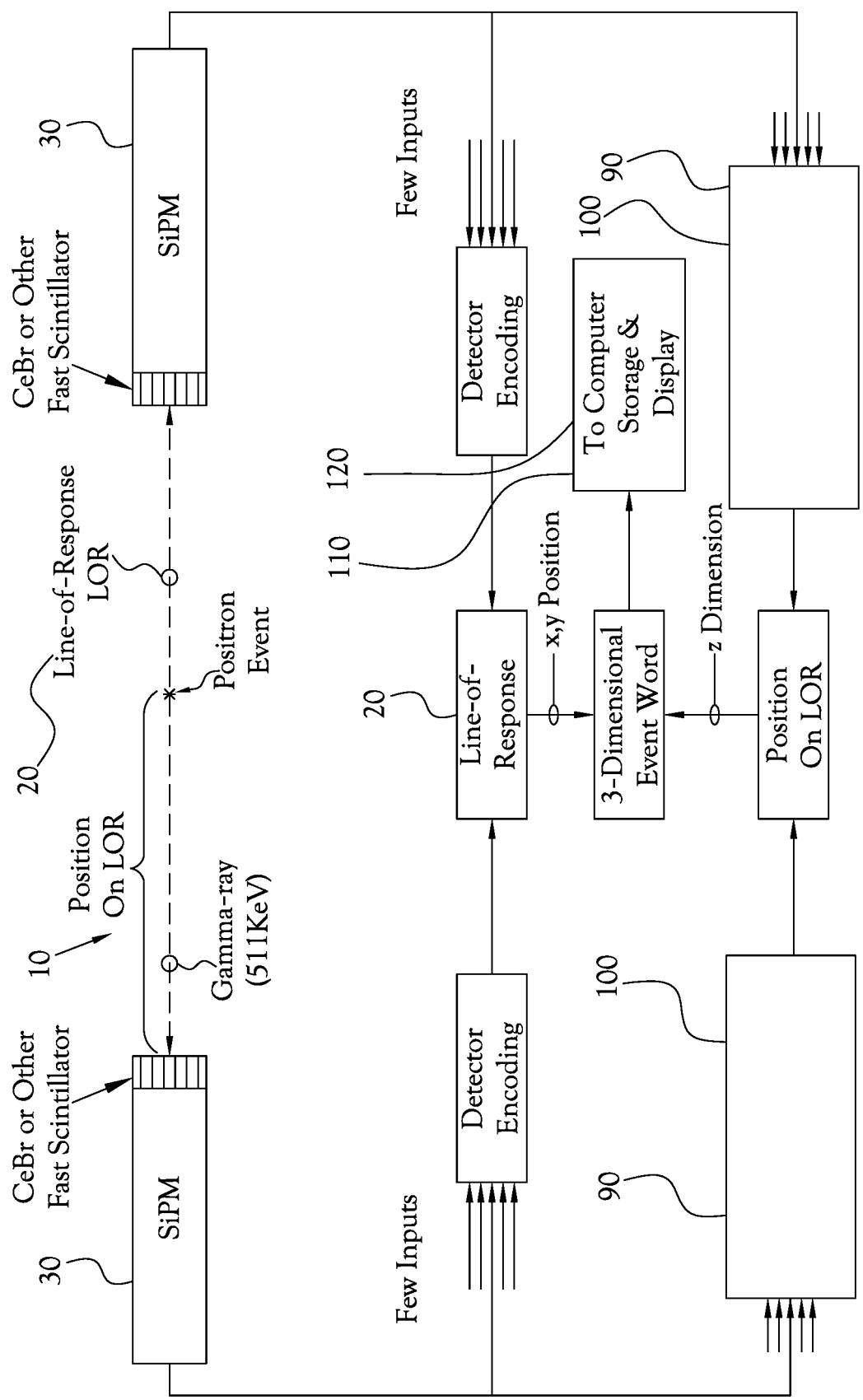
FIGS. 6A, 6B, and 6C are more detailed views of a TPET according to exemplary embodiments of the present general inventive concept.
Figure 6B:
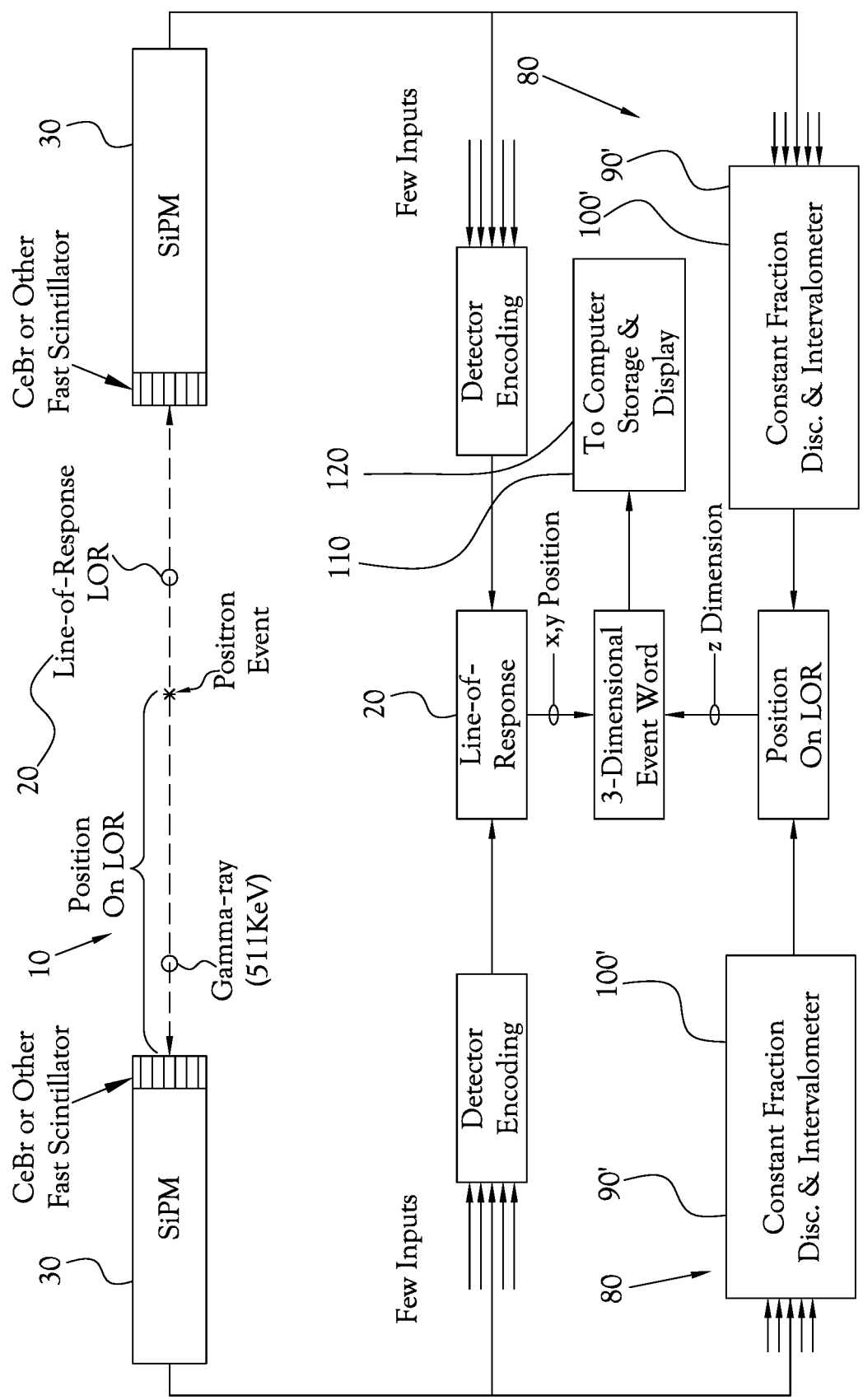
Figure 6C:
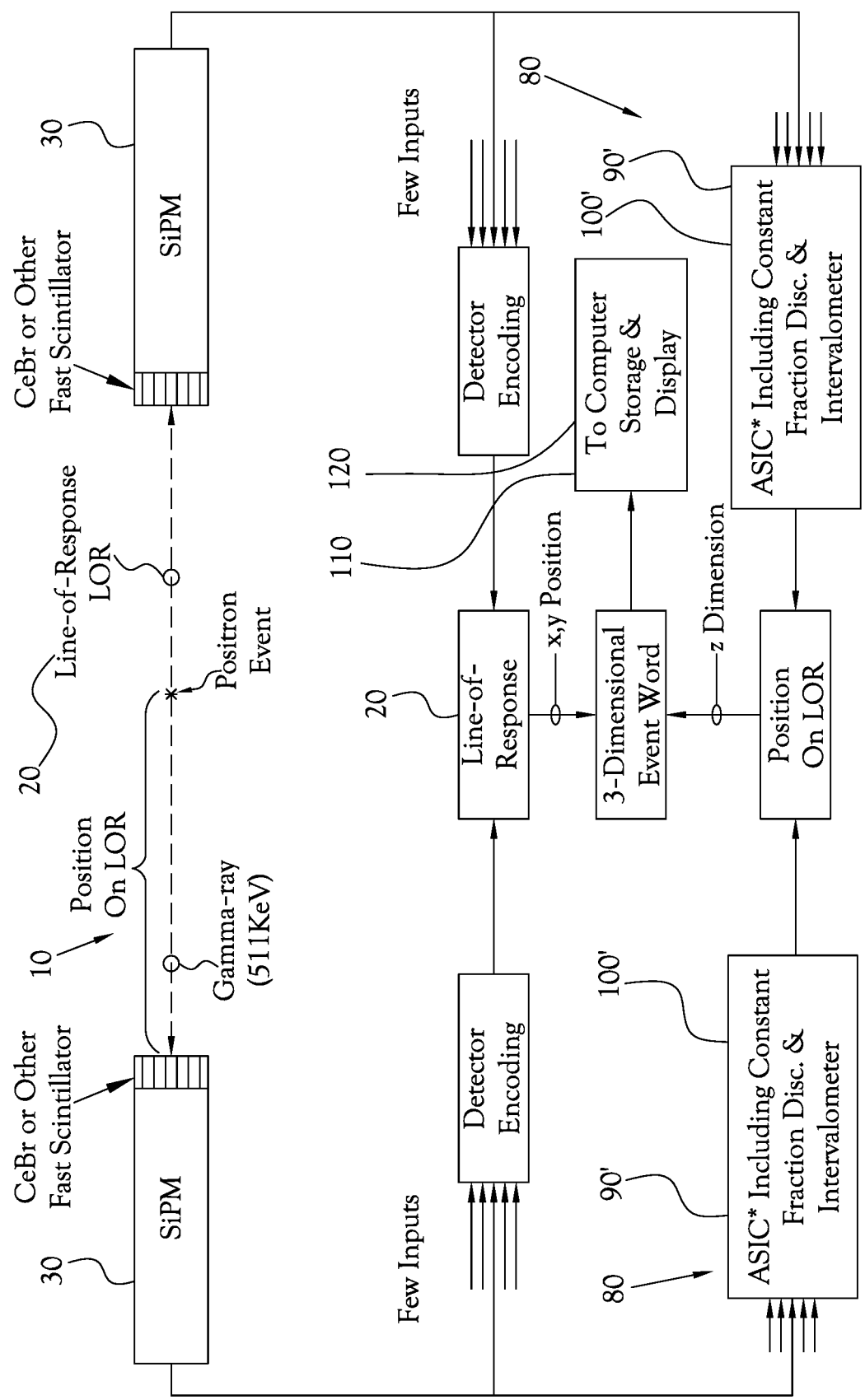
Figure 7A:
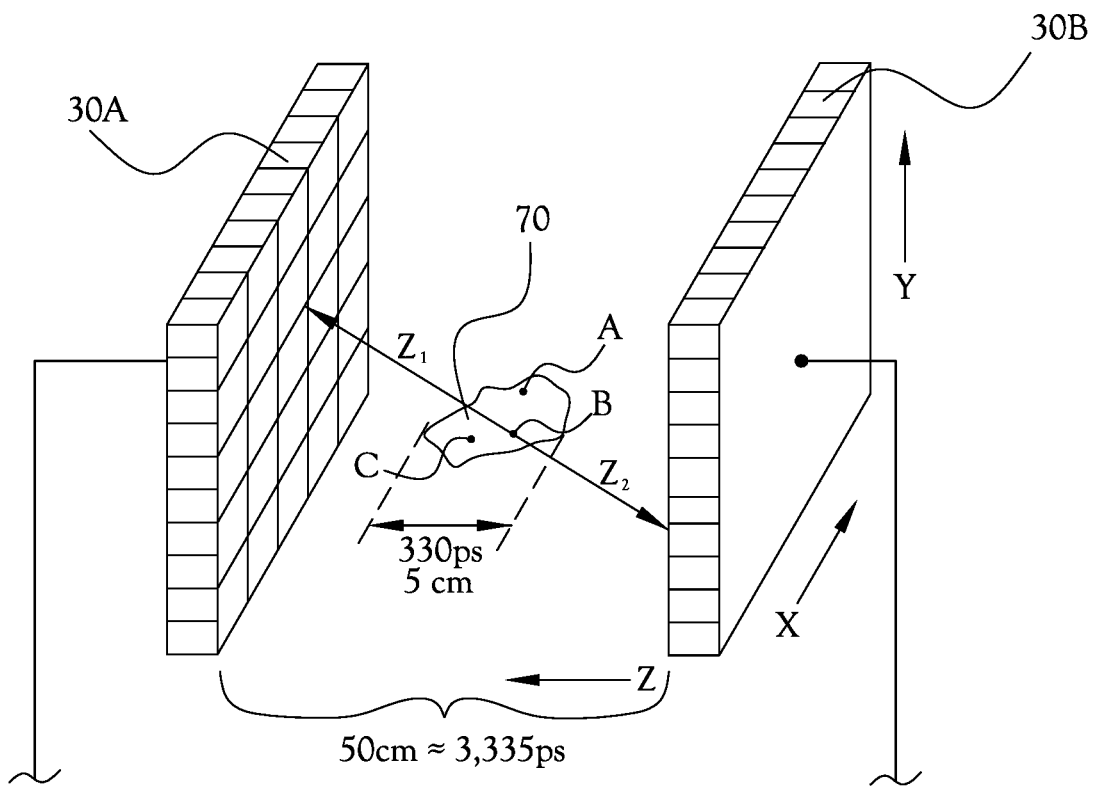
FIGS. 7A and 7B illustrate schematic views of the process of capturing a three-dimensional image, and determining the X, Y, and Z coordinates, in 7A, or vector coordinates in 7B, of the respective positron events, with a two-detector system according to an exemplary embodiment of the present general inventive concept.

A Time-Resolved Positron Emission Tomography, TPET, system 10 capable of providing real-time, high resolution, three-dimensional imagery is illustrated in FIGS. 5, 6A, 6B, 6C, 7A, 7B, and 8. It will be understood that in state-of-the-art PET imagery, the normal LOR 20 is determined by standard block detectors 30A and 30B, which, as will be understood, are diametrically opposed to one another, and measure the gamma ray position, in both the X and Y coordinates, 40 and 50 respectively, in two-dimensional space as schematically illustrated in FIG. 7A. FIG. 5 depicts a TPET imaging system of the present general inventive concept. FIG. 5 represents the TPET imaging system showing the required two parallel plates of detectors, 30A and 30B, having typically a factor of ten fewer detectors than the prior art.

Figure 7B:
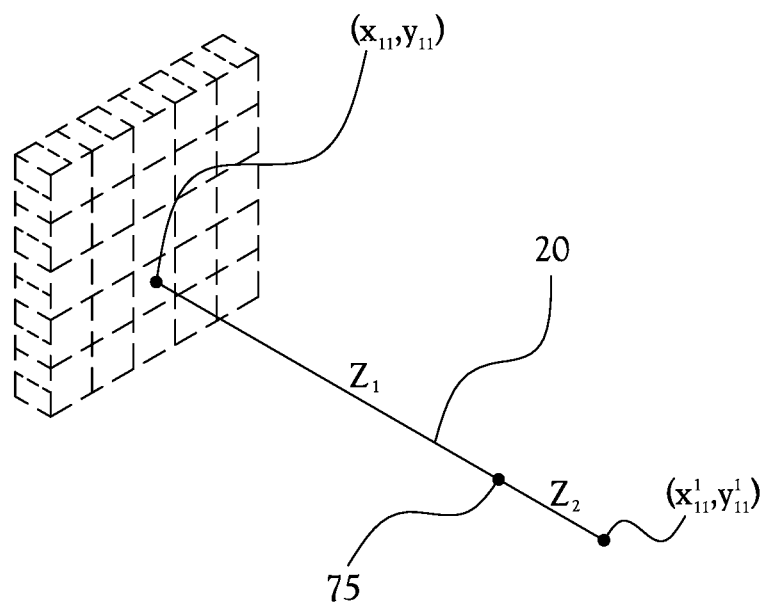

In FIGS. 7A and 7B, the positron events, such as positron event 75 in FIG. 7A, that is occurring in the organ 70, is illustrated schematically. Referring to FIGS. 7A and 7B, the arithmetic for a single positron event at Point B, in FIG. 7A, can be represented as follows:

$$Z_{LOR} = Z_1 + Z_2$$

$$\Delta T = (Z_1 - Z_2)k$$

Where k=6.66 ps/mm (i.e. the inverse of the speed of light)

$$\frac{\Delta T}{k} = (Z_1 - Z_2)$$

$$Z_{LOR} = Z_1 + Z_2$$

By adding these two equations, the result is:

$$\frac{\Delta T}{k} + Z_{LOR} = 2Z_1$$

$$\therefore Z_1 = \frac{\Delta T}{k} + \frac{Z_{LOR}}{2}$$

$Z_1$ is the location along the LOR.

$Z_{LOR}$ is calculated and obtained from a look-up table.

The time difference, $\Delta T$, between the arrival times of coincident gamma rays detected by block detectors 30A and 30B determines the position of the positron event along the LOR 20. FIG. 7A shows the results of the basic measurement including the X, Y and Z directions. The X and Y positions are determined by the conventional block detectors and the Z direction is determined by the difference in arrival times of the two gamma rays in opposing detectors. With the Z time measurement and the X and Y determination, the point in space where the event originated is determined and can be displayed. In other words, the third dimension, Z coordinate 60 in an XYZ coordinate system, see, e.g., FIG. 7A, is provided by the time measurement of the travel of the gamma ray and by calculating the difference between the time one gamma ray is detected and when the second coincident gamma ray is detected.

Figure 8:
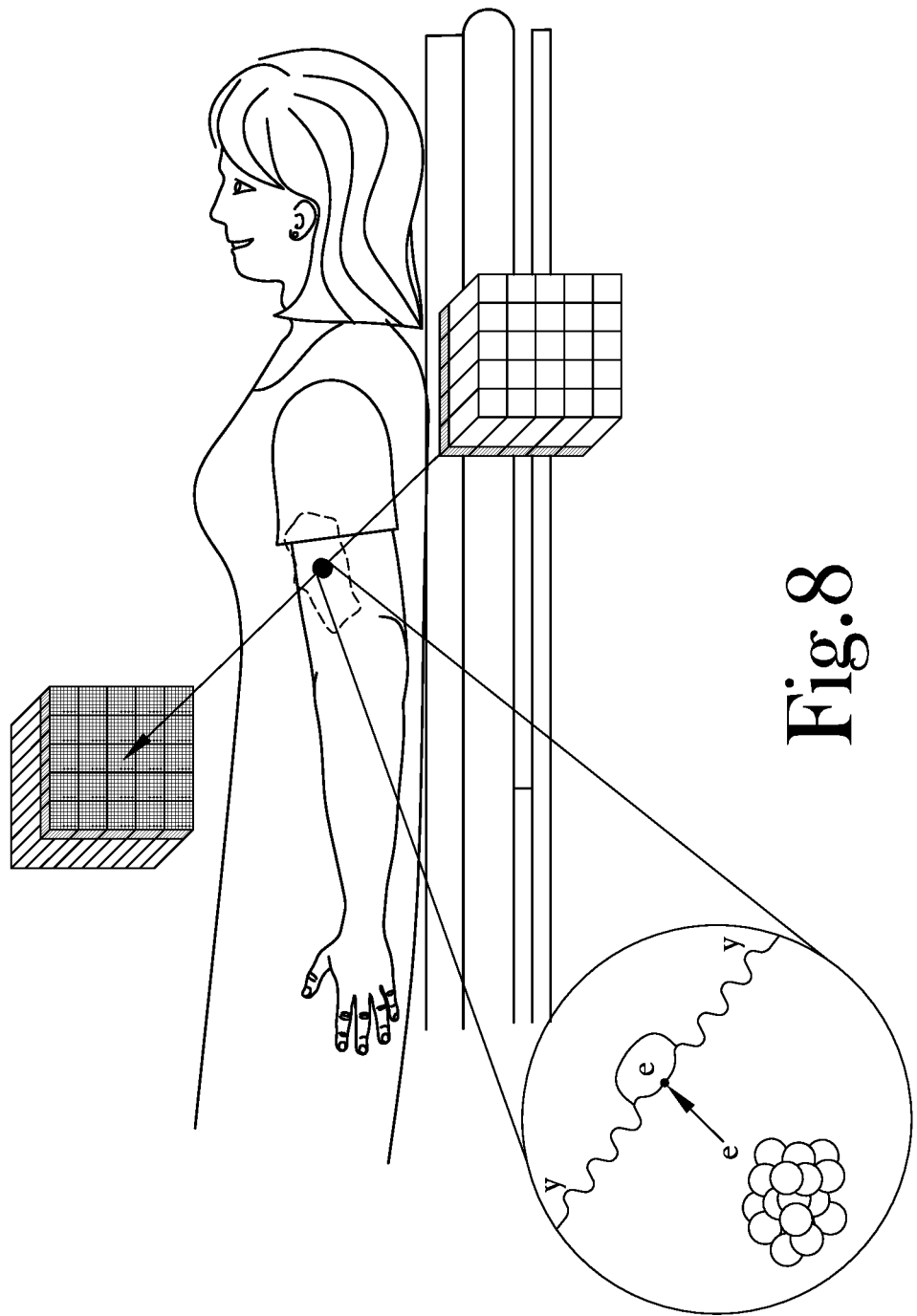
FIG. 8 is a schematic view of an exemplary embodiment of a simpler TPET Imaging detector array system.

While measuring the gamma ray, i.e., positron event, position and the position itself has been discussed in Cartesian terms, regarding X, Y, and Z coordinates, in an exemplary embodiment, vector analysis, i.e., vector algebra, would be employed to determine the location of a positron event, such as positron event 75 in FIG. 7B. In this regard, processing circuitry will determine the position of the positron event 75 when the detector element of each detector plate, 30A and 30B, is measured and the time difference, $\Delta T$, between the respective detector elements is measured. Referring to FIG. 7B, each vector will be defined with the X,Y and $X^1,Y^1$ data points. In an exemplary embodiment, an exemplary array will be composed of approximately 40 detectors in the horizontal, or X, direction and 40 detectors in the vertical, or Y, direction. This produces an array having 1,600 detectors in each detector plate. These two detector plates are diametrically opposed to one another and are, in an exemplary embodiment, as illustrated in FIG. 8, parallel to one another. With that element count, there will be $(1,600)^2$ Lines of Response, ("LORs"). Each LOR will be defined before system use with the location of each memory pixel along the LOR vector. With such arrangement, a computer, having cubic memory would have the intersection of each LOR with each memory pixel stored in its memory. When the time difference, $\Delta T$, is measured and the LOR is identified, the location is then identified for each positron event such as positron event 75. The computer then uses vector analysis, instead of Cartesian coordinates, for forming the three-dimensional image. The three points of a hypothetical vector would be defined, or expressed, as follows:

Vector: $(X_{25}, Y_{35})$ $(X_{15}, Y_{20})$, $\Delta T=2.33$ ns

Thus, referring back to FIG. 7A, the vectors for positron events A, B, and C, originating in organ 70 would be expressed as follows:

Point A: $(X_{21}, Y_{23})$, $\Delta T=250$ ps
Point B: $(X_{22}, Y_{21})$, $\Delta T=350$ ps
Point C: $(X_{18}, Y_{19})$, $\Delta T=500$ ps These events are accumulated in a small memory data acquisition module 120 for analysis and continued display in imaging system 110. It should be understood that the vector analysis and the $\Delta T$ are calculated and displayed in the imaging system 110 gamma event by gamma event in real time, as each gamma event is detected, without the need for either time-consuming image reconstruction or a CT scan for correction of attenuation. In an exemplary embodiment, block detectors 30A and 30B could be either silicon photomultiplier, (SiPM), or conventional photomultipliers.

In an exemplary embodiment, the TPET imaging system 10 of the present general inventive concept utilizes an SiPM for the optical detector and a very high yield photon, fast scintillator such as $CeBr_3$ (35,000 photons per 511 KeV) or $LaBr_3$. With the $CeBr_3$ scintillator, the stopping power for gamma rays is worse than the usual PET scintillators; but this loss in stopping power is offset by the high inherent efficiency of the TPET. For this TPET design the position resolution along the LOR 20 is calculated as follows:

The theoretical resolution of a single exponential scintillator decay is given by:

$$T_{(FWHM)} = \frac{\tau x 2.35}{Nx\mathcal{E}} = 17x\frac{2.35}{35,000x0.1} = 11.4 \text{ ps}$$

where τ is decay time, N is number of scintillation photons, and ε is the quantum efficiency of optical detector and FWHM is full width half maximum.

The time resolution of the SiPM:

$$T(fwhm)=25 \text{ ps}$$

For one channel:

$T=27.5$ ps

Because there are two channels:

$$T_s=1.41 \times 27.5 = 38.8$$

This resolution in time corresponds to 5.8 mm resolution along the LOR 20.

Referring to FIG. 6C, in order to provide this time measurement gamma event-by-gamma event, i.e., in real time, and in a manner that requires detection of significantly fewer events than traditional PET, in an exemplary embodiment of the TPET imaging system 10, further electronic circuitry 90, in FIG. 6A, which decreases the time walk to an insignificant contribution of the overall time resolution, is utilized.

The electronic circuitry 90, in FIG. 6A, for decreasing the time walk described above, functions to have the trigger for time measurement occur at a fixed fraction of the input pulse. This is accomplished by placing an input pulse on two input lines, delaying, inverting, and amplifying the one input line. The resulting negative, delayed and amplified input is added back to the original input pulse. The result is a bipolar pulse with a zero crossing time which will occur at the same time of a fixed fraction of the pulse. As the amplitude of the pulse changes, the zero crossing time will remain.

Secondly, time measuring electronic circuitry 100, in FIG. 6A, is provided which consists of a digital clock which counts the ticks on an oscillator between a start and a stop signal. In this regard, further electronic circuitry 100 measures the arrival time of each photon in the annihilation process with picosecond resolution.

The time measuring electronic circuitry 100, in FIG. 6A, functions to count the ticks of an oscillator between a start and stop signal. The limitation of the conventional, state-of-the-art system is that the accuracy is plus or minus (±) one tick of the oscillator. In order to obtain higher accuracy, the time from the start pulse to the oscillator is measured using an analog time-to-pulse height converter and this time is added back to the conventional pulse counter. The same process is used to eliminate the inaccuracy at the stop signal.

Additionally, the phase between the start and the oscillator is measured by a digital TAC and the difference between the oscillator and the stop signal is also measured with a digital TAC. The most significant digits of the clock are provided by the digital TAC and added sequentially to the word containing the ticks of the oscillator. If the desired measurement is between a start and the oscillator, which is the case for TPET operation, only one of the TAC interpolators is used to measure the time of arrival of one of the 511 KeV gamma rays.

Figure 1D:
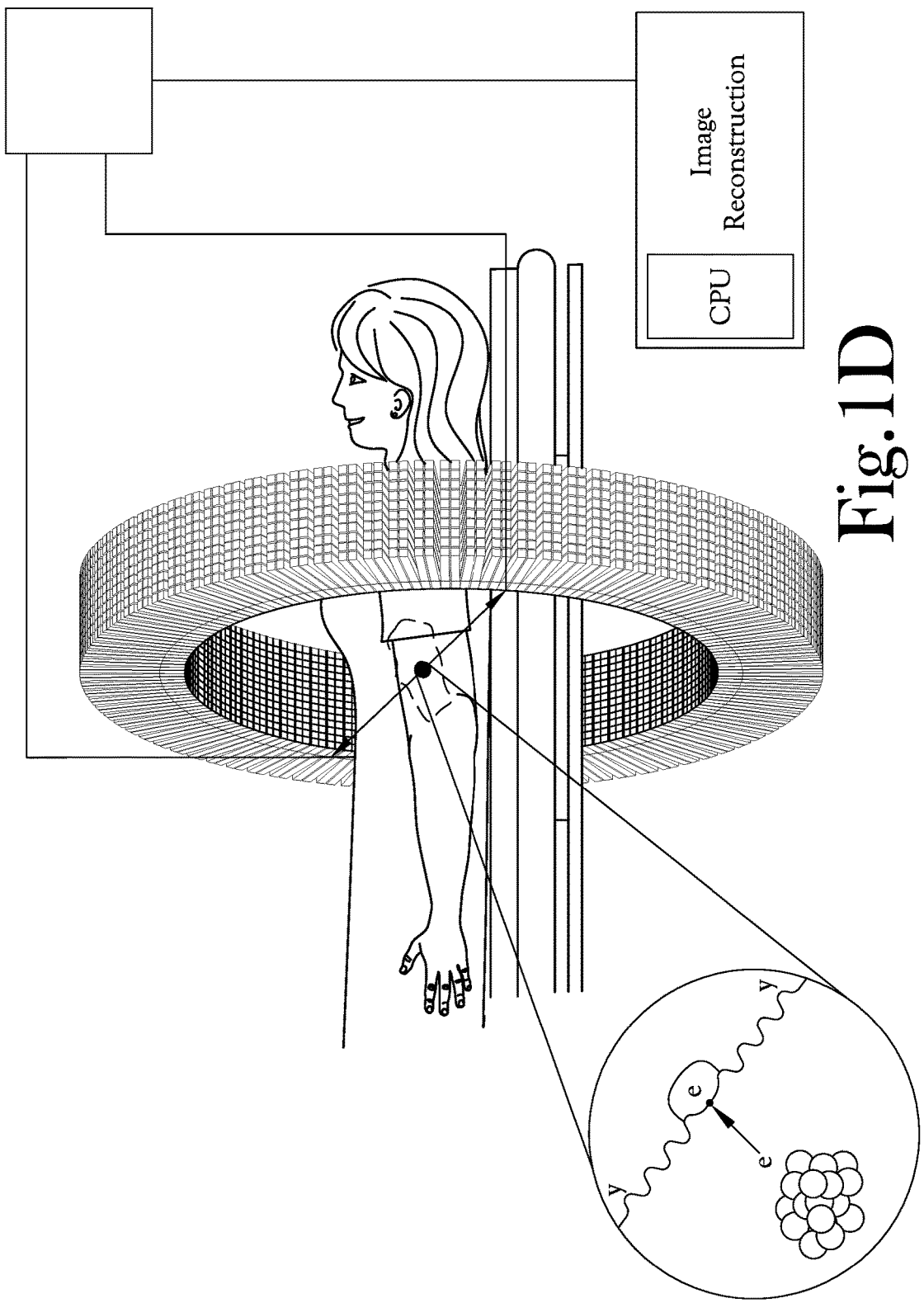
FIG. 1D is a schematic view of a prior art PET Imaging system having a detector Ring and reliant upon image reconstruction.
Figure 2A:
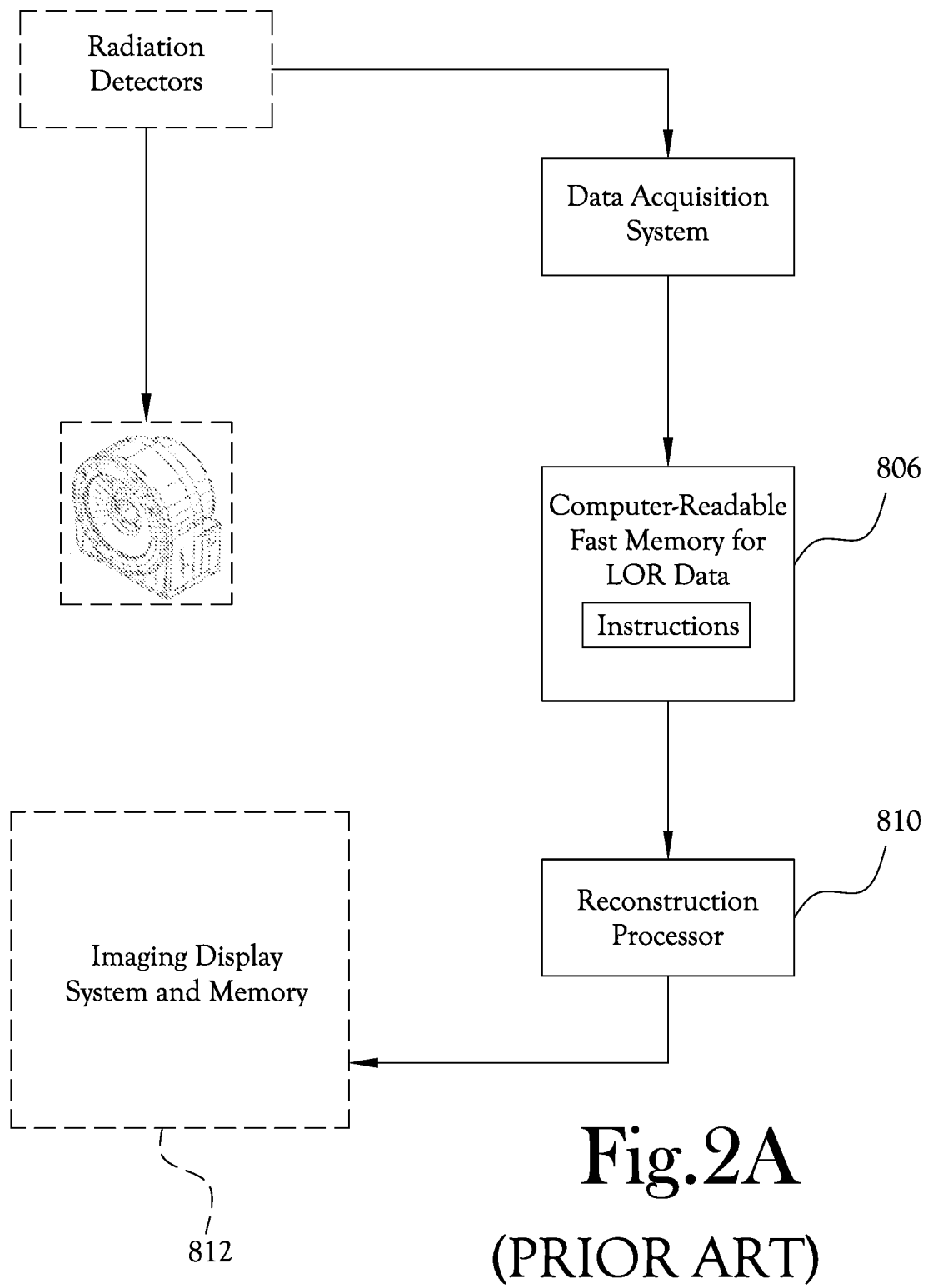
FIG. 2A illustrates, in schematic view, a conventional PET imaging system as exemplified in U.S. Published Patent Application No. 2013/0009063.
Figure 2B:
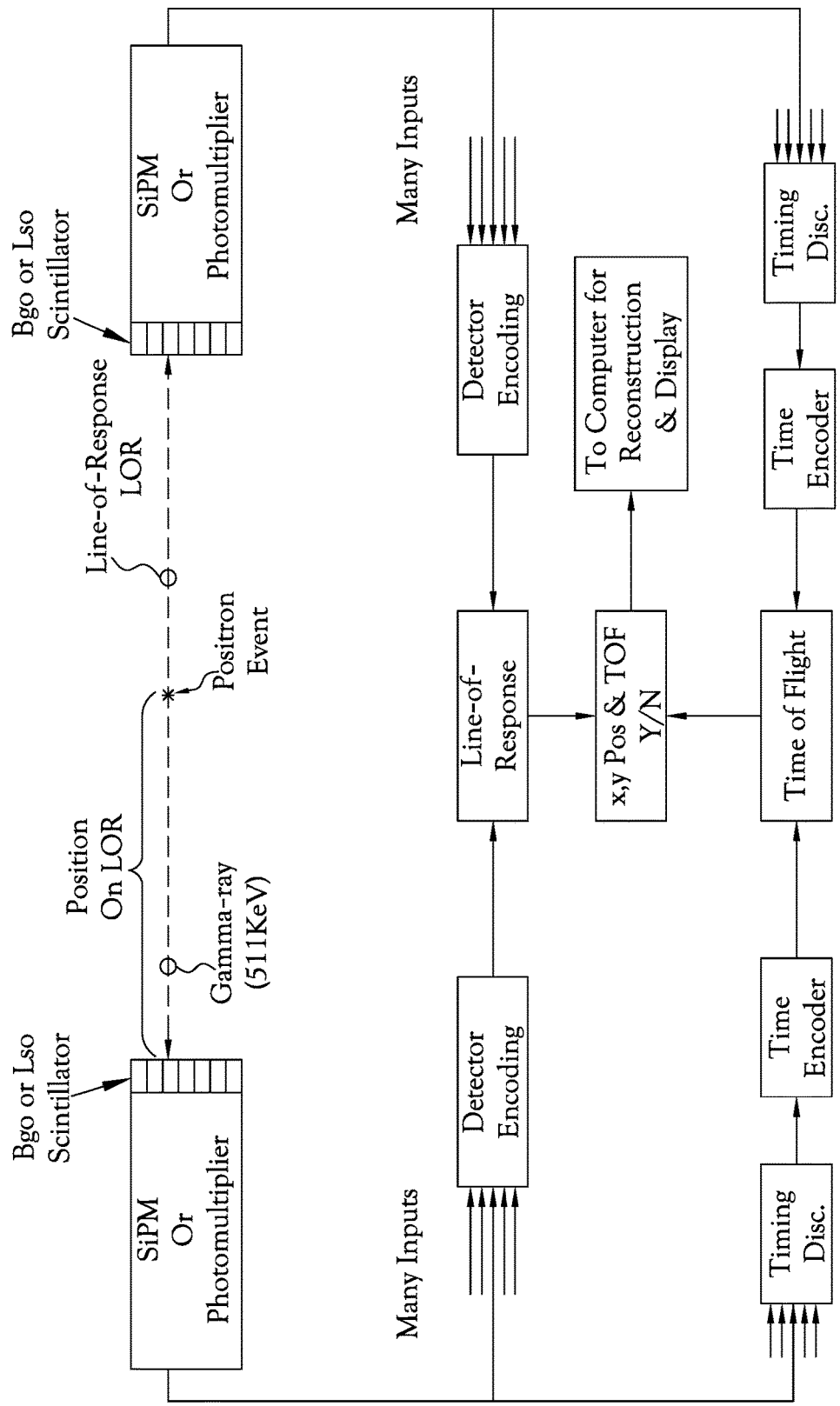
FIG. 2B further illustrates, in schematic view, a conventional PET imaging system.
Figure 4:
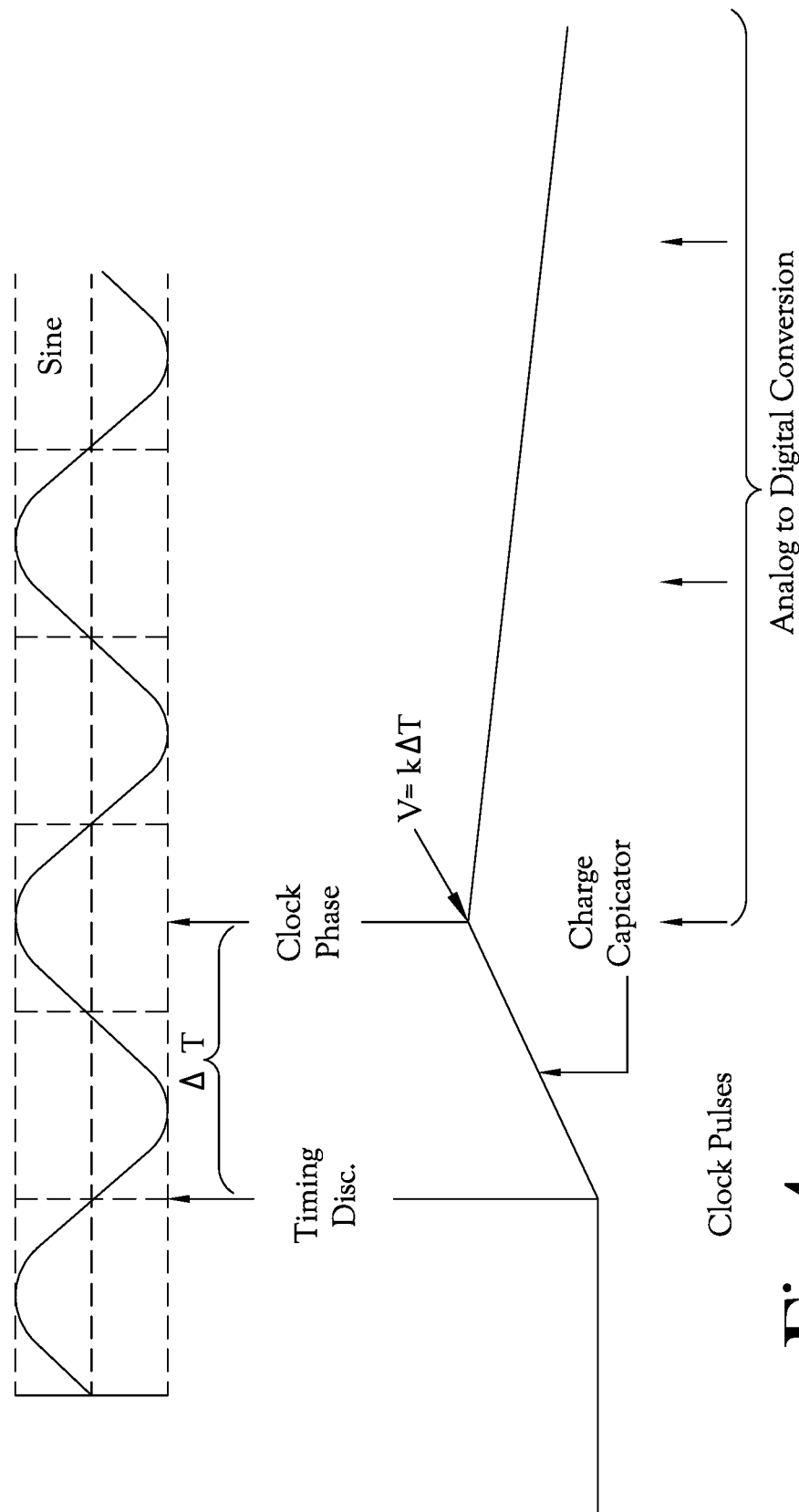
FIG. 4 is a chart illustrating the operational process of applicant's Digital Intervalometer as utilized in an exemplary embodiment of the present general inventive concept.

In an exemplary embodiment, the electronic circuitry for decreasing the time walk is provided by a Constant Fraction Discriminator, ("CFD"), 90'. The use of a CFD 90' decreases the time walk to an insignificant contribution of the overall time resolution of the TPET imaging system 10. Further, in an exemplary embodiment of the TPET imaging system 10 of the present general inventive concept, this picosecond resolution time-measuring electronic circuitry is defined by a Digital Intervalometer 100'. With this time measurement system, the arrival time of each photon in the annihilation process is recorded with respect of a clock frequency with picosecond resolution. With the proper design and the use of this time measurement, the time resolution will be insignificant to the overall measurement. The Digital Intervalometer 100' utilizes the TAC to interpolate between the start signal and the clock. Then the TAC is converted to a digital signal by standard Analog-to-Digital ("ADC") method and this digital signal is added to the end of the digital clock word to form the time measurement. The stop signal is generated by an arbitrary fixed signal synchronized with the clock. This process is illustrated in FIG. 4. In this regard, it is known in the art that if no interpolation is used, the measured time resolution using only the counting of the clock pulses will result in a plus and minus 125 ps for a clock frequency of 8 GHz. Prior experimentation and research in the art has attempted to compensate for various issues with state-of-the-art timing discriminators and time encoders by doing the interpolation off-line and in so doing by attempting to measure the input rise-time and extrapolating the phase. This is not a practical approach in a clinical, diagnostic application. In this regard, the clinical diagnostic environment requires a TPET imaging system 10 that is capable of producing high resolution, three-dimensional imagery gamma event-by-gamma event without image reconstruction.

This is the case for the TPET imaging system 10. The arrival time of each gamma ray event is measured and digitally stored and then digitally compared with all other measured events. Any two measured events that occur within a few picoseconds of each other will be defined as a positron annihilation event and used to form the three-dimensional image. In an exemplary embodiment, this approach requires significantly fewer gamma events, thus requiring fewer detectors, and gives rise to a gamma event-by-gamma event high resolution three-dimensional imagery. This results in a TPET imaging system 10 that is more efficient and more economical to produce than a conventional PET imaging system.

In summary, in an exemplary embodiment, the TPET imaging system 10 of the present general inventive concept includes the use of electronic circuitry for measuring the difference of arrival time in order to determine the position of a positron event along an LOR 20, in a manner that allows for event-by-event, high resolution imagery and that also reduces time walk. In an exemplary embodiment of the TPET imaging system, this further electronic circuitry is defined by both a Constant Fraction Discriminator 90 and a Digital Intervalometer 100. While the Constant Fraction Discriminator 90 and the Digital Intervalometer 100 could be used as discrete chip sets or discrete integrated circuits, in an exemplary embodiment, the Constant Fraction Discriminator 90 and the Digital Intervalometer 100 are combined in an Application Specific Integrated Circuit, ("ASIC"), 80. While an exemplary embodiment that utilizes a Constant Fraction Discriminator and a Digital Intervalometer to perform these functions has been described, it will be understood that other electronic circuitry adapted to perform these functions could also be utilized especially as computing efficiency and power continue to increase.

By measuring the arrival time of each photon in the annihilation process and calculating the difference in arrival times at the opposed detector blocks, third dimension can be provided, resulting in a TPET imaging system 10. In an exemplary embodiment, the TPET imaging system of the present general inventive concept has the capability of meeting or even exceeding the image resolution of existing PET systems and will contribute three additional very important characteristics to the system. The TPET imaging system 10 of the present general inventive concept will be, comparatively, very simple and therefore very inexpensive to manufacture compared to full ring modern PET tomographs.

As seen in FIG. 8, because the TPET system of the present disclosure utilizes significantly fewer detector blocks than a state-of-the-art PET Imaging Ring, (80 pixels compared to 18,000 pixels), the TPET imaging system 10 of the present general inventive concept can provide artifact free images without covering the entire body as is required by conventional PET imaging systems. This feature makes the TPET imaging system 10 of the present general inventive concept feasible for individual organ imaging such as breast, heart, prostate, and imaging lungs for Coronavirus damage. This feature allows a design with a very small number of detectors. The third main benefit is that the images are formed as each gamma event is detected, i.e., in an event-by-event manner, variously referred to herein as being "in real-time" without the inherent delay required by image reconstruction or attenuation correction. This feature gives rise to event-by-event, real-time image comparisons of multiple organs, thereby giving the clinician/diagnostician greater understanding of the relationships of multiple organ systems, for example of the brain and heart. Also, the real-time feature provides the clinician a view of cancer sites as the site is being treated with radiation or other means such as Proton Therapy. With these characteristics, the TPET imaging system 10 of the present general inventive concept has the potential of replacing state-of-the-art PET systems and represents a major breakthrough for medical imaging in general. Further, as will be recognized by those skilled in the art, the Avalanche Photodiode not only improves the time resolution of scintillator systems; but its resistance to magnetic fields allows the TPET imaging system 10 of the present general inventive concept to be used in a combined TPET and Magnetic Resonance Imaging ("MRI") system for acquiring MRI and TPET images simultaneously in a single device, and will allow the TPET imaging system to operate in relatively high radiation fields. A fourth feature is that the TPET uses only one view, while in comparison the traditional PET uses many views around the patient. With only one view, calculated attenuation for the emitted gamma-rays can be achieved with good accuracy. This feature eliminates need for a CT scan for attenuation correction. This further reduces the cost and complexity of the TPET imaging system 10.

Various exemplary embodiments of the present general inventive concept may provide an event-by-event, high resolution, three-dimensional positron emission tomography encoder system which includes a plurality of cooperating pairs of diametrically opposed scintillation detectors adapted for receiving gamma rays from a positron event, electronic circuitry in electronic communication with each pair of said diametrically opposed scintillation detectors for determining the two-dimensional position of the positron event occurring between each pair of detectors, each event producing said gamma rays which travel along a line of response extending between cooperating pairs of detectors, and further electronic circuitry for measuring the difference between the arrival times of coincident gamma rays from a positron event detected by said diametrically opposed scintillation detectors along said line of response thereby enabling determination of the third dimension along said line of response of said positron event to produce an event-by-event, real-time, high resolution, three dimensional positron emission tomographic image without the necessity of performing image reconstruction or performing a CT scan for attenuation correction. The further electronic circuitry may include a Constant Fraction Discriminator and a Digital Intervalometer. In embodiments in which a Constant Fraction Discriminator and a Digital Intervalometer are utilized, such can be utilized as discrete chip sets or, in an exemplary embodiment, embedded on an application specific integrated circuit. The digital intervalometer may utilize a time amplitude converter. The pairs of diametrically opposed scintillation detectors may each include a silicon photomultiplier operating in an avalanche photodiode mode. The pairs of diametrically opposed scintillation detectors may include a channel multiplier.

Various exemplary embodiments of the present general inventive concept may provide a process for capturing event-by-event, high resolution, three-dimensional positron emission tomography imagery, in real-time, which includes providing a selected number of cooperating pairs of diametrically opposed scintillation detectors adapted for receiving coincident gamma rays from a positron event, determining a two-dimensional position of the positron event producing said gamma ray photons, determining a line of response for each cooperating pair of detectors of said coincident gamma rays, and detection of and measuring, in real-time, the time of said coincident gamma rays being detected by a cooperating pair of diametrically opposed scintillation detectors along said line of response in order to determine the third dimension along said line of response of said positron event, thereby producing a real-time, high resolution, three dimensional positron emission tomographic image. The process for capturing real-time, high resolution, three-dimensional positron emission tomography imagery may include a Constant Fraction Discriminator and a Digital Intervalometer, and may include these specific integrated circuits utilized as discrete chip sets or, in an exemplary embodiment, embedded on an application specific integrated circuit. The digital intervalometer may utilize a time-to-amplitude converter. The cooperating pairs of diametrically opposed scintillation detectors may each include a silicon photomultiplier and/or a channel multiplier. The cooperating pairs of diametrically opposed scintillation detectors may include a channel multiplier.

Various exemplary embodiments of the present general inventive concept may provide an event-by-event, real-time, high resolution, three-dimensional positron emission tomography encoder system which includes a plurality of cooperating pairs of diametrically opposed scintillation detectors adapted for receiving gamma rays from a positron event, electronic circuitry in electronic communication with each pair of said diametrically opposed scintillation detectors for determining the two-dimensional position of the positron event occurring between each pair of detectors, each event producing said gamma rays which travel along a line of response extending between cooperating pairs of detectors. Further electronic circuitry may include a Constant Fraction Discriminator and a Digital Intervalometer utilized either as discrete chip sets or, in an exemplary embodiment, embedded on an application specific integrated circuit for measuring the difference between the arrival times of coincident gamma rays from a positron event detected by said diametrically opposed scintillation detectors along said line of response thereby enabling determination of the third dimension along said line of response of said positron event to produce a real-time, high resolution, three dimensional positron emission tomographic image without image reconstruction. The digital intervalometer may utilize a time amplitude converter. The pairs of diametrically opposed scintillation detectors may each include a silicon photomultiplier operating in an avalanche photodiode mode. The pairs of diametrically opposed scintillation detectors may include a channel multiplier.

Various exemplary embodiments of the present general inventive concept may provide a process for capturing event-by-event, high resolution, three-dimensional positron emission tomography imagery, in real-time, which includes providing a selected number of cooperating pairs of diametrically opposed scintillation detectors adapted for receiving coincident gamma rays from a positron event, determining a two-dimensional position of the positron event producing said gamma ray photons, determining a line of response for each cooperating pair of detectors of said coincident gamma rays, and detection of and measuring, in real-time, the time of said coincident gamma rays being detected by a cooperating pair of diametrically opposed scintillation detectors along said line of response in order to determine the third dimension along said line of response of said positron event using a Constant Fraction Discriminator and a Digital Intervalometer utilized as discrete chip sets or, in an exemplary embodiment, embedded on an application specific integrated circuit, thereby producing a real-time, high resolution, three dimensional positron emission tomographic image. The digital intervalometer may utilize a time-to-amplitude converter. The pairs of diametrically opposed scintillation detectors may include a silicon photomultiplier and/or a channel multiplier. The pairs of diametrically opposed scintillation detectors may include a channel multiplier.

While the present general inventive concept has been illustrated by description of several embodiments and while the illustrative embodiments have been described in detail, it is not the intention of the applicant to restrict or in any way limit the scope of the appended claims to such detail. Additional modifications will readily appear to those skilled in the art. The present general inventive concept in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned present general inventive concept, what is claimed is:

1. An encoder system to form three-dimensional Positron Emission Tomography Images, event-by-event in real-time and without perfoming image reconstruction and without requiring CT scans to correct attenuation of the Positron Emission Tomography signal, said encoder system comprising:
a plurality of cooperating pairs of opposed gamma ray detectors adapted for detecting a positron event;
electronic circuitry in electronic communication with each pair of said opposed gamma ray detectors for determining a two-dimensional position of the positron event occurring between each pair of opposed gamma ray detectors, each event producing said gamma rays which travel along a line of response extending between cooperating pairs of detectors; and
further electronic circuitry for reducing time walk associated with leading edge discriminators and for measuring a difference between the arrival times of coincident gamma rays from said positron event detected by said opposed gamma ray detectors along said line of response with picosecond resolution thereby enabling determination of a third dimensional position of the positron event along said line of response thereby producing an event-by-event, real-time, high resolution, three-dimensional positron emission tomographic image without performing an image reconstruction.

2. The event-by-event encoder system of claim 1, wherein said further electronic circuitry for substantially reducing time walk associated with leading edge discriminators and for measuring a difference between the arrival times of coincident gamma rays includes a constant fraction discriminator and a digital intervalometer.

3. The event-by-event encoder system of claim 2, wherein said constant fraction discriminator and said digital intervalometer are embedded on an application specific integrated circuit.

4. The event-by-event encoder system of claim 2, wherein said digital intervalometer utilizes a time amplitude converter.

5. The event-by-event encoder system of claim 1, wherein said pairs of opposed gamma ray detectors are each comprised of a silicon photomultiplier operating in an avalanche photodiode mode.

6. The event-by-event encoder system of claim 5, wherein said pairs of opposed gamma ray detectors are arranged in opposed parallel plate arrays.

7. The event-by-event encoder system of claim 1, wherein said pair of opposed gamma ray detectors are comprised of a channel multiplier.

8. A process for forming three-dimensional Positron Emission Tomography Images, event-by-event in real-time and without performing image reconstruction and without requiring CT scans to correct attenuation of the Positron Emission Tomography signal, said process comprising:
providing a selected number of cooperating pairs of opposed gamma ray detectors adapted for receiving coincident gamma rays from a positron event;
determining a two-dimensional position of the positron event producing said gamma ray photons;
determining a line of response for each cooperating pair of opposed gamma ray detectors of said coincident gamma rays;
reducing time walk associated with leading edge discriminators; and
detecting and measuring with picosecond resolution, gamma event-by-gamma event, a time difference of said coincident gamma rays being detected by a cooperating pair of opposed gamma ray detectors along said line of response in order to determine a third dimensional position of the positron event along said line of response, thereby producing an event-by-event, high resolution, three-dimensional positron emission tomographic image without performing an image reconstruction.

9. The process of claim 8 wherein in said step of detection of and measuring, on a gamma event by gamma event basis, a time of said coincident gamma rays being detected includes use of a constant fraction discriminator and a digital intervalometer.

10. The process of claim 9, wherein said constant fraction discriminator and said digital intervalometer are embedded on an application specific integrated circuit.

11. The process of claim 9, wherein said digital intervalometer utilizes a time-to-amplitude converter.

12. The process of claim 8, wherein the cooperating pairs of opposed gamma ray detectors are selected from a group consisting of a silicon photomultiplier and a channel multiplier.

13. The process of claim 8, wherein a pair of opposed gamma ray detectors are comprised of a channel multiplier.

14. The process of claim 13, wherein said pairs of opposed gamma ray detectors are arranged in opposed parallel plate arrays.

15. An encoder system to form three-dimensional Positron Emission Tomography Images, event-by-event in real-time and without performing image reconstruction and without requiring CT scans to correct attenuation of the Positron Emission Tomography signal, said encoder system comprising:
  a plurality of cooperating pairs of opposed gamma ray detectors adapted for detecting a positron event;
  electronic circuitry in electronic communication with each pair of said opposed gamma ray detectors for determining a two-dimensional position of the positron event occurring between each pair of opposed gamma ray detectors, each event producing said gamma rays which travel along a line of response extending between cooperating pairs of detectors; and
  further electronic circuitry for reducing time walk associated with leading edge discriminators and for measuring a difference between the arrival times of coincident gamma rays from said positron event detected by said opposed gamma ray detectors along said line of response with picosecond resolution thereby enabling determination of a third dimensional position of the positron event along said line of response thereby producing an event-by-event, high resolution, three-dimensional positron emission tomographic image without performing an image reconstruction, said further electronic circuitry including a time amplitude converter.

16. The real-time, high resolution, three-dimensional positron emission tomography encoder system of claim 15, wherein said further electronic circuitry is embedded on an application specific integrated circuit.

17. The real-time, high resolution, three-dimensional positron emission tomography encoder system of claim 15, wherein said pairs of opposed gamma ray detectors are each comprised of a silicon photomultiplier operating in an avalanche photodiode mode.

18. The real-time, high resolution, three-dimensional positron emission tomography encoder system of claim 15, wherein said pair of opposed gamma ray detectors are comprised of a channel multiplier.

19. The real-time, high resolution, three-dimensional positron emission tomography encoder system of claim 15, wherein said wherein said pairs of opposed gamma ray detectors are arranged in opposed parallel plate arrays.

20. A real-time, high resolution, three-dimensional positron emission tomography encoder system to form three-dimensional Positron Emission Tomography Images, event-by- event in real-time and without performing image reconstruction and without requiring CT scans to correct attenuation of the Positron Emission Tomography signal, which comprises:
  a plurality of cooperating pairs of opposed gamma ray detectors adapted for detecting a positron event;
  electronic circuitry in electronic communication with each pair of said opposed gamma ray detectors for determining a two-dimensional position of the positron event occurring between each pair of opposed gamma ray detectors, each event producing said gamma rays which travel along a line of response extending between cooperating pairs of detectors; and
  further electronic circuitry including a constant fraction discriminator and a digital intervalometer for measuring a difference between the arrival times of coincident gamma rays from said positron event detected by said opposed gamma ray detectors along said line of response thereby enabling determination of a third dimensional position of said positron event along said line of response thereby producing a real-time, high resolution, three dimensional positron emission tomographic image without a necessity of performing image reconstruction.

21. The real-time, high resolution, three-dimensional positron emission tomography encoder system of claim 20, wherein said constant fraction discriminator and said digital intervalometer are embedded on an application specific integrated circuit.

22. The real-time, high resolution, three-dimensional positron emission tomography encoder system of claim 20, wherein said pair of opposed gamma ray detectors are each comprised of a silicon photomultiplier operating in an avalanche photodiode mode.

23. The real-time, high resolution, three-dimensional positron emission tomography encoder system of claim 20, wherein said pair of opposed gamma ray detectors are comprised of channel multiplier.

24. The real-time, high resolution, three-dimensional positron emission tomography encoder system of claim 20, wherein said wherein said pairs of opposed gamma ray detectors are arranged in opposed parallel plate arrays.

25. A real-time, high resolution, three-dimensional positron emission tomography encoder system which comprises:
  a plurality of cooperating pairs of opposed gamma ray detectors adapted for receiving gamma rays from a positron event;
  electronic circuitry in electronic communication with each pair of said opposed gamma ray detectors for determining the two-dimensional position of the positron event occurring between each pair of opposed gamma ray detectors, each event producing said gamma rays which travel along a line of response extending between cooperating pairs of detectors; and
  further electronic circuitry including a constant fraction discriminator and a digital intervalometer for measuring a difference between the arrival times of coincident gamma rays at each of said opposed gamma ray detectors from a positron event detected by said opposed gamma ray detectors along said line of response wherein said digital intervalometer utilizes a time-to-amplitude converter, whereby a position of said positron event along said line of response is determined, thereby enabling determination of a third dimensional position of said positron event along said line of response to produce a real-time, high resolution, three dimensional positron emission tomographic image without a necessity of performing image reconstruction.

26. The real-time, high resolution, three-dimensional positron emission tomography encoder system of claim 25, wherein said pairs of opposed gamma ray detectors are each comprised of a silicon photomultiplier operating in an avalanche photodiode mode.

27. The real-time, high resolution, three-dimensional positron emission tomography encoder system of claim 25, wherein said pair of opposed gamma ray detectors are comprised of a channel multiplier.

28. The real-time, high resolution, three-dimensional positron emission tomography encoder system of claim 25, wherein said constant fraction discriminator and said digital intervalometer are embedded on an application specific integrated circuit.

29. The real-time, high resolution, three-dimensional positron emission tomography encoder system of claim 25, wherein said wherein said pairs of opposed gamma ray detectors are arranged in opposed parallel plate arrays.

* * * * *